(12) United States Patent
DuBridge et al.

(10) Patent No.: US 8,283,170 B2
(45) Date of Patent: Oct. 9, 2012

(54) IMMUNOGLOBULIN DISPLAY VECTORS

(75) Inventors: Robert DuBridge, Belmont, CA (US); Wenge Zhang, Mountain View, CA (US); Susan Rhodes, San Mateo, CA (US)

(73) Assignee: Abbott Biotherapeutics Corp., Redwood City, CA (US)

( * ) Notice: Subject to any disclaimer, the term of this patent is extended or adjusted under 35 U.S.C. 154(b) by 0 days.

(21) Appl. No.: 13/090,065

(22) Filed: Apr. 19, 2011

(65) Prior Publication Data

US 2011/0250611 A1 Oct. 13, 2011

Related U.S. Application Data

(62) Division of application No. 12/263,272, filed on Oct. 31, 2008, now Pat. No. 7,947,495.

(51) Int. Cl.
*C12N 15/85* (2006.01)
*C12N 15/63* (2006.01)

(52) U.S. Cl. ................ 435/455; 435/320.1; 435/325

(58) Field of Classification Search .................. None
See application file for complete search history.

(56) References Cited

U.S. PATENT DOCUMENTS

| 7,569,362 B2 | 8/2009 | Prentice |
| 7,732,195 B2 | 6/2010 | Akamatsu et al. |
| 7,858,559 B2 | 12/2010 | Zauderer et al. |
| 2005/0059082 A1 | 3/2005 | Breitling et al. |
| 2005/0196755 A1 | 9/2005 | Zauderer et al. |
| 2011/0008883 A1 | 1/2011 | Akamatsu et al. |

FOREIGN PATENT DOCUMENTS

| EP | 1340088 B1 | 1/2007 |
| WO | 03/029456 A1 | 4/2003 |
| WO | 2007/131774 A1 | 11/2007 |

OTHER PUBLICATIONS

Brezinsky, S.C.G. et al. "A simple method for enriching populations of transfected CHO cells for cells of higher specific productivity." J Immunol Methods. Jun. 1, 2003;277(1-2):141-55.
Browne, Susan M. and Mohamed Al-Rubeai. "Selection methods for high-producing mammalian cell lines." Trends Biotechnol. Sep. 2007;25(9):425-32.
Li, Jiandong et al. "A comparative study of different vector designs for the mammalian expression of recombinant IgG antibodies." J Immunol Methods. Jan. 10, 2007;318(1-2):113-24.
Mattanovich, Diethard and Nicole Borth. "Applications of cell sorting in biotechnology." Microb Cell Fact. Mar. 21, 2006;5:12.
International Search Report and Written Opinion of the International Searching Authority for PCT/US2008/082131, dated Sep. 29, 2009.
Restriction Requirement for U.S. Appl. No. 12/263,272, mailed on Feb. 16, 2010, pp. 8.
Non-Final Office Action for U.S. Appl. No. 12/263,272, mailed on Jun. 15, 2010, pp. 5.
Notice of Allowance for U.S. Appl. No. 12/263,272, mailed on Jan. 20, 2011, pp. 8.

*Primary Examiner* — Celine Qian

(57) ABSTRACT

Disclosed are mammalian expression vectors for expressing simultaneous expression of immunoglobulins as both a secreted and cell surface bound form.

15 Claims, 6 Drawing Sheets

FIG. 4

| | Sequence | Base to Base Alignment | | | | | | | | | | | | | | |
|---|---|---|---|---|---|---|---|---|---|---|---|---|---|---|---|---|
| WT Sequence | CTCTGTCCCTACAG | | C | T | C | T | G | T | C | C | C | T | A | C | A | G |
| Primer for Library Construction (S=G,C B=G,C,T) | | | S | B | S | B | S | G | B | S | S | B | A | C | A | G |
| Sequence-1 | GTCCGCGCGGACAG | G | | G | T | C | C | G | C | G | C | G | G | A | C | A | G |
| Sequence-2 | GCCGGGGGGTACAG | G | | C | C | G | G | G | G | G | G | G | T | A | C | A | G |
| Sequence-3 | GCCCGGGGGTACAG | G | | C | C | C | G | G | G | G | G | G | T | A | C | A | G |
| Sequence-4 | GGGGGTGGCGACAG | | | G | G | G | G | G | T | G | G | C | G | A | C | A | G |
| Sequence-5 | GTCTGGGGCACAG | | | G | T | C | T | G | G | G | G | C | | A | C | A | G |
| Sequence-6 | CTGTGGGCCGCACAG | | | C | T | G | T | G | G | G | C | C | G | C | A | C | A | G |
| Sequence-7 | CGGGGGGGTACAG | | | C | G | G | G | G | G | G | G | G | T | A | C | A | G |
| Sequence-8 | CCGGGTGCGACAG | | | C | C | G | G | G | T | G | C | G | | A | C | A | G |
| Sequence-9 | GGCCGTGGGCACAG | | | G | G | C | C | G | T | G | G | G | C | A | C | A | G |
| Sequence-10 | CGTGGTGCGACAG | | | C | G | T | G | G | T | G | C | G | | A | C | A | G |
| Sequence-11 | GGGCGGGGTACAG | | | G | G | G | C | G | G | G | G | T | | A | C | A | G |
| Sequence-12 | GCGTGGCCGTACAG | | | G | C | G | T | G | G | C | C | G | T | A | C | A | G |
| Sequence-13 | CGTCGGCCCCGACAG | C | | G | T | C | G | G | C | C | C | C | G | A | C | A | G |
| Sequence-14 | CCGTGGGGCGACAG | | | C | C | G | T | G | G | G | G | C | G | A | C | A | G |
| Summary | Frequency of T | | 4 | | 4 | | | 4 | | | | 5 | | | | | |
| | Enrichment of G/C at these Four Positions | | | | | | | | | | | | | | | | |

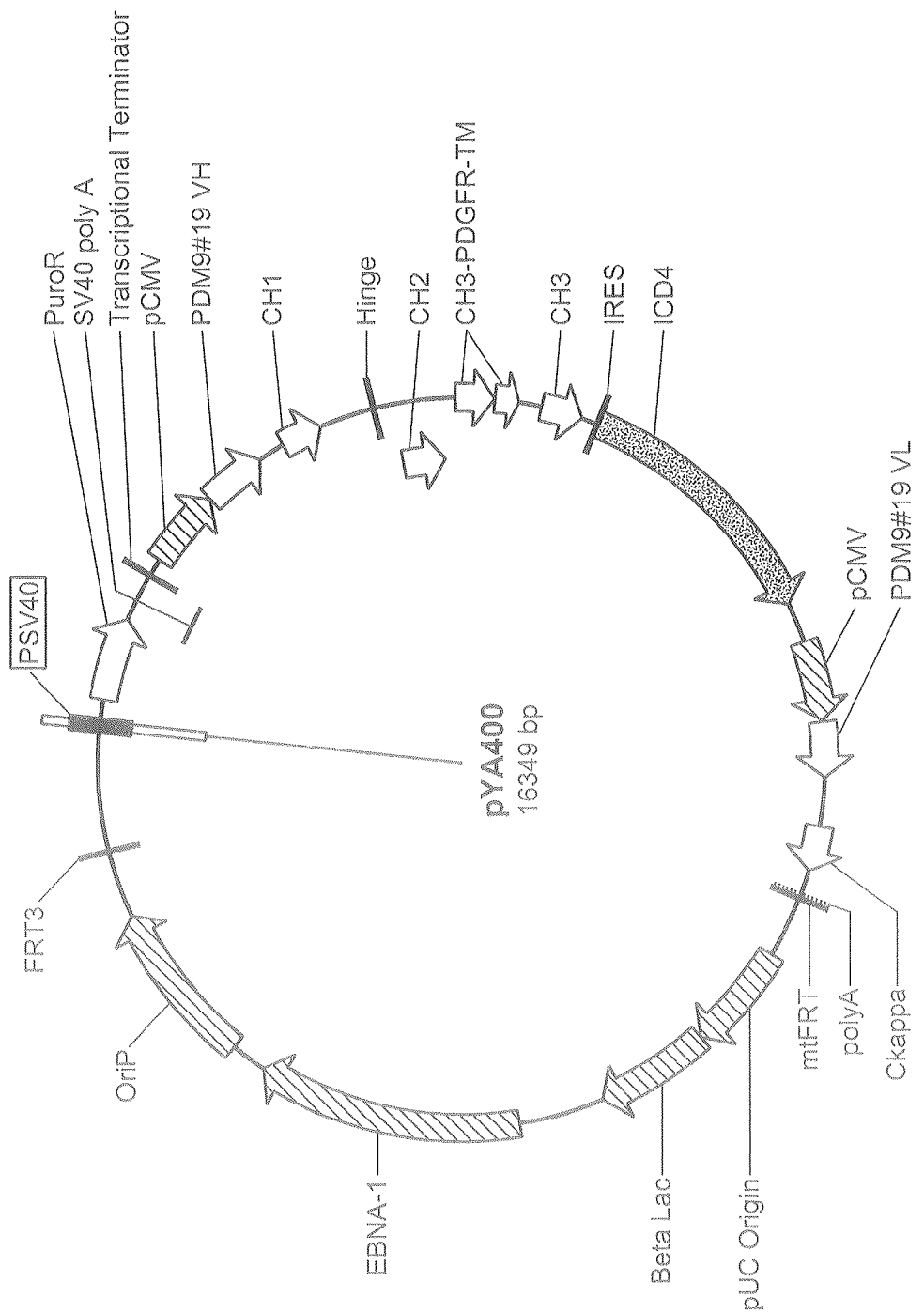

SEQUENCE LISTING

```
<160> NUMBER OF SEQ ID NOS: 55

<210> SEQ ID NO 1
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 1
sbsbgbsssb acag                                                      14

<210> SEQ ID NO 2
<211> LENGTH: 20
<212> TYPE: PRT
<213> ORGANISM: Homo sapiens

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 26
<212> TYPE: PRT
<213> ORGANISM: Homo sapiens

<400> SEQUENCE: 3

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 4
<211> LENGTH: 14
<212> TYPE: DNA
<213> ORGANISM: Homo sapiens

<400> SEQUENCE: 4
ctctgtccct acag                                                      14

<210> SEQ ID NO 5
<211> LENGTH: 49
<212> TYPE: PRT
<213> ORGANISM: Artificial Sequence
<220> FEATURE:
<223> OTHER INFORMATION: Synthetic polypeptide

<400> SEQUENCE: 5
```

Ala Val Gly Gln Asp Thr Gln Glu Val Ile Val Pro His Ser Leu
1               5                   10                  15

Pro Phe Lys Val Val Ile Ser Ala Ile Leu Ala Leu Val Val Leu
            20                  25                  30

Thr Ile Ile Ser Leu Ile Ile Leu Ile Met Leu Trp Gln Lys Pro
            35                  40                  45

Arg

<210> SEQ ID NO 6
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 6

Lys Pro Pro Glu Asp Pro Pro Asp Ser Lys Asn Thr Leu Val Leu Phe
1               5                   10                  15

Gly Ala Gly Phe Gly Ala Val Ile Thr Val Val Ile Val Val Ile
            20                  25                  30

Ile Lys Cys Phe Cys Lys His Arg Ser Cys Phe Arg Arg Asn Glu Ala
            35                  40                  45

Ser Arg Glu Thr Asn Asn Ser Leu Thr Phe Gly Pro Glu Glu Ala Leu
    50                  55                  60

Ala Glu Gln Thr Val Phe Leu
65                  70

<210> SEQ ID NO 7
<211> LENGTH: 48
<212> TYPE: DNA
<213> ORGANISM: Artificial Sequence
<220> FEATURE:
<223> OTHER INFORMATION: Synthetic primer

<400> SEQUENCE: 7
atttggccat taattaacac catggctgtc ctggggctgc ttctctgc                48

<210> SEQ ID NO 8
<211> LENGTH: 42
<212> TYPE: DNA
<213> ORGANISM: Artificial Sequence
<220> FEATURE:
<223> OTHER INFORMATION: Synthetic primer

<400> SEQUENCE: 8
tcgaattcct cgaggccatt cttacctgag gagacggtga cc                      42

<210> SEQ ID NO 9
<211> LENGTH: 50
<212> TYPE: DNA
<213> ORGANISM: Artificial Sequence
<220> FEATURE:
<223> OTHER INFORMATION: Synthetic primer

<400> SEQUENCE: 9
aggttcgaag agctcagatc tgaattcctc gaggccattc ttacctgagg              50

<210> SEQ ID NO 10
<211> LENGTH: 36
<212> TYPE: DNA
<213> ORGANISM: Artificial Sequence
<220> FEATURE:
<223> OTHER INFORMATION: Synthetic primer

```
<400> SEQUENCE: 10
attctcgagg ctttctgggg caggccaggc ctgacc                              36

<210> SEQ ID NO 11
<211> LENGTH: 33
<212> TYPE: DNA
<213> ORGANISM: Artificial Sequence
<220> FEATURE:
<223> OTHER INFORMATION: Synthetic primer

<400> SEQUENCE: 11
attgaattcc tcagggcaga gggtgggccg agc                                 33

<210> SEQ ID NO 12
<211> LENGTH: 29
<212> TYPE: DNA
<213> ORGANISM: Artificial Sequence
<220> FEATURE:
<223> OTHER INFORMATION: Synthetic primer

<400> SEQUENCE: 12
aggaattcag agtgaccgct gtaccaacc                                      29

<210> SEQ ID NO 13
<211> LENGTH: 45
<212> TYPE: DNA
<213> ORGANISM: Artificial Sequence
<220> FEATURE:
<223> OTHER INFORMATION: Synthetic primer

<400> SEQUENCE: 13
tcctgcgtgt cctggcccac agctttaccc ggagacaggg agagg                    45

<210> SEQ ID NO 14
<211> LENGTH: 45
<212> TYPE: DNA
<213> ORGANISM: Artificial Sequence
<220> FEATURE:
<223> OTHER INFORMATION: Synthetic primer

<400> SEQUENCE: 14
tctccctgtc tccgggtaaa gctgtgggcc aggacacgca ggagg                    45

<210> SEQ ID NO 15
<211> LENGTH: 42
<212> TYPE: DNA
<213> ORGANISM: Artificial Sequence
<220> FEATURE:
<223> OTHER INFORMATION: Synthetic primer

<400> SEQUENCE: 15
agcgggggct tgccggccgt cgcctaacgt ggcttcttct gc                       42

<210> SEQ ID NO 16
<211> LENGTH: 39
<212> TYPE: DNA
<213> ORGANISM: Artificial Sequence
<220> FEATURE:
<223> OTHER INFORMATION: Synthetic primer

<400> SEQUENCE: 16
ttggcagaag aagccacgtt aggcgacggc cggcaagcc                           39

<210> SEQ ID NO 17
<211> LENGTH: 35
```

```
<212> TYPE: DNA
<213> ORGANISM: Artificial Sequence
<220> FEATURE:
<223> OTHER INFORMATION: Synthetic primer

<400> SEQUENCE: 17
attagatcta gggcagcgct gggtgcttta tttcc                                 35

<210> SEQ ID NO 18
<211> LENGTH: 31
<212> TYPE: DNA
<213> ORGANISM: Artificial Sequence
<220> FEATURE:
<223> OTHER INFORMATION: Synthetic primer

<400> SEQUENCE: 18
attagatctt acgtgccaag catcctcgtg c                                     31

<210> SEQ ID NO 19
<211> LENGTH: 34
<212> TYPE: DNA
<213> ORGANISM: Artificial Sequence
<220> FEATURE:
<223> OTHER INFORMATION: Synthetic primer

<400> SEQUENCE: 19
attagatctc ccgtggggtg cgagggccac atgg                                  34

<210> SEQ ID NO 20
<211> LENGTH: 26
<212> TYPE: DNA
<213> ORGANISM: Artificial Sequence
<220> FEATURE:
<223> OTHER INFORMATION: Synthetic primer

<400> SEQUENCE: 20
attgagctca gggcagcgct gggtgc                                           26

<210> SEQ ID NO 21
<211> LENGTH: 26
<212> TYPE: DNA
<213> ORGANISM: Artificial Sequence
<220> FEATURE:
<223> OTHER INFORMATION: Synthetic primer

<400> SEQUENCE: 21
attgagctcc ggaccgctaa ttccgg                                           26

<210> SEQ ID NO 22
<211> LENGTH: 33
<212> TYPE: DNA
<213> ORGANISM: Artificial Sequence
<220> FEATURE:
<223> OTHER INFORMATION: Synthetic primer

<400> SEQUENCE: 22
aggttcgaac tcattaaact tgtattttaa tgg                                   33

<210> SEQ ID NO 23
<211> LENGTH: 28
<212> TYPE: DNA
<213> ORGANISM: Artificial Sequence
<220> FEATURE:
<223> OTHER INFORMATION: Synthetic primer

<400> SEQUENCE: 23
aggttcgaaa ggcgttacat aacttacg                                         28
```

<210> SEQ ID NO 24
<211> LENGTH: 43
<212> TYPE: DNA
<213> ORGANISM: Artificial Sequence
<220> FEATURE:
<223> OTHER INFORMATION: Synthetic primer

<400> SEQUENCE: 24
atccatggtg gcctgcaggg gatctgagtc cggtagcgct agc        43

<210> SEQ ID NO 25
<211> LENGTH: 39
<212> TYPE: DNA
<213> ORGANISM: Artificial Sequence
<220> FEATURE:
<223> OTHER INFORMATION: Synthetic primer

<400> SEQUENCE: 25
actcagatcc cctgcaggcc accatggatt ttcaggtgc            39

<210> SEQ ID NO 26
<211> LENGTH: 42
<212> TYPE: DNA
<213> ORGANISM: Artificial Sequence
<220> FEATURE:
<223> OTHER INFORMATION: Synthetic primer

<400> SEQUENCE: 26
tcagagttta gaattgcggc cgcttaggaa agtgcactta cg         42

<210> SEQ ID NO 27
<211> LENGTH: 46
<212> TYPE: DNA
<213> ORGANISM: Artificial Sequence
<220> FEATURE:
<223> OTHER INFORMATION: Synthetic primer

<400> SEQUENCE: 27
agtgcacttt cctaagcggc cgcaattcta aactctgagg gggtcg     46

<210> SEQ ID NO 28
<211> LENGTH: 34
<212> TYPE: DNA
<213> ORGANISM: Artificial Sequence
<220> FEATURE:
<223> OTHER INFORMATION: Synthetic primer

<400> SEQUENCE: 28
aggttcgaag tgcaaagatt cactttattt attc                 34

<210> SEQ ID NO 29
<211> LENGTH: 42
<212> TYPE: DNA
<213> ORGANISM: Artificial Sequence
<220> FEATURE:
<223> OTHER INFORMATION: Synthetic primer

<400> SEQUENCE: 29
ttcggaatag gaacttcgtg caaagattca ctttatttat tc         42

<210> SEQ ID NO 30
<211> LENGTH: 42
<212> TYPE: DNA
<213> ORGANISM: Artificial Sequence
<220> FEATURE:
<223> OTHER INFORMATION: Synthetic primer

```
<400> SEQUENCE: 30 tacctttga agaataggaa cttcggaata ggaacttcgt gc                          42

<210> SEQ ID NO 31
<211> LENGTH: 34
<212> TYPE: DNA
<213> ORGANISM: Artificial Sequence
<220> FEATURE:
<223> OTHER INFORMATION: Synthetic primer

<400> SEQUENCE: 31
aggttcgaag ttcctatacc ttttgaagaa tagg                                   34

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
attactagta tttattgccc aagg                                              24

<210> SEQ ID NO 33
<211> LENGTH: 41
<212> TYPE: DNA
<213> ORGANISM: Artificial Sequence
<220> FEATURE:
<223> OTHER INFORMATION: Synthetic primer

<400> SEQUENCE: 33
aacttcggaa taggaacttt cccaccccat gagctgtcac g                           41

<210> SEQ ID NO 34
<211> LENGTH: 40
<212> TYPE: DNA
<213> ORGANISM: Artificial Sequence
<220> FEATURE:
<223> OTHER INFORMATION: Synthetic primer

<400> SEQUENCE: 34
tactaagtag agaataggaa cttcggaata ggaactttcc                             40

<210> SEQ ID NO 35
<211> LENGTH: 37
<212> TYPE: DNA
<213> ORGANISM: Artificial Sequence
<220> FEATURE:
<223> OTHER INFORMATION: Synthetic primer

<400> SEQUENCE: 35
attgatatcg aagttcctat actaagtaga gaatagg                                37

<210> SEQ ID NO 36
<211> LENGTH: 30
<212> TYPE: DNA
<213> ORGANISM: Artificial Sequence
<220> FEATURE:
<223> OTHER INFORMATION: Synthetic primer

<400> SEQUENCE: 36
attgaattca gagtgaccgc tgtaccaacc                                        30

<210> SEQ ID NO 37
<211> LENGTH: 26
```

-continued

<210> SEQ ID NO 37
<211> LENGTH: 26
<212> TYPE: DNA
<213> ORGANISM: Artificial Sequence
<220> FEATURE:
<223> OTHER INFORMATION: Synthetic primer

<400> SEQUENCE: 37
attaagcttc cagaggaact gcttcc					26

<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
acagggcagc cccgagaacc acagg					25

<210> SEQ ID NO 39
<211> LENGTH: 38
<212> TYPE: DNA
<213> ORGANISM: Artificial Sequence
<220> FEATURE:
<223> OTHER INFORMATION: Synthetic primer

<400> SEQUENCE: 39
aacsbsbgbs ssbacagggc agccccgaga accacagg					38

<210> SEQ ID NO 40
<211> LENGTH: 41
<212> TYPE: DNA
<213> ORGANISM: Artificial Sequence
<220> FEATURE:
<223> OTHER INFORMATION: Synthetic primer

<400> SEQUENCE: 40
agagtgaccg ctgtaccaac sbsbgbsssb acagggcagc c					41

<210> SEQ ID NO 41
<211> LENGTH: 28
<212> TYPE: DNA
<213> ORGANISM: Artificial Sequence
<220> FEATURE:
<223> OTHER INFORMATION: Synthetic primer

<400> SEQUENCE: 41
aggaattcag agtgaccgct gtaccaac					28

<210> SEQ ID NO 42
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 42
gtgcgcgcgg acag					14

<210> SEQ ID NO 43
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 43 gccgggggggg tacag					15

```
<210> SEQ ID NO 44
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 44
gcccgggggg tacag                                                    15

<210> SEQ ID NO 45
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 45 gggggggtggc gacag                                                   15

<210> SEQ ID NO 46
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 46
gtgtgggggc acag                                                     14

<210> SEQ ID NO 47
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 47
ctgtgggccg cacag                                                    15

<210> SEQ ID NO 48
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 48
cggggggggt acag                                                     14

<210> SEQ ID NO 49
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 49
ccgggtgcgc acag                                                     14

<210> SEQ ID NO 50
<211> LENGTH: 14
<212> TYPE: DNA
<213> ORGANISM: Artificial Sequence
<220> FEATURE:
<223> OTHER INFORMATION: Synthetic oligonucleotide
```

```
<400> SEQUENCE: 50
ggccgtgggc acag                                                         14

<210> SEQ ID NO 51
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 51
cgtggtgcgc acag                                                         14

<210> SEQ ID NO 52
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 52
ggggcgggta cag                                                          13

<210> SEQ ID NO 53
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 53
gcgtggccgt acag                                                         14

<210> SEQ ID NO 54
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 54
cgtcggcccc gacag                                                        15

<210> SEQ ID NO 55
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 55
ccgtggggcg acag                                                         14
```

IMMUNOGLOBULIN DISPLAY VECTORS

1. CROSS REFERENCE TO RELATED APPLICATIONS

The present application is a divisional of U.S. application Ser. No. 12/263,272, filed Oct. 31, 2008, which claims benefit under 35 U.S.C. §119(e) to application Ser. No. 60/984,650, filed on Nov. 1, 2007, both incorporated herein in their entirety by reference.

2. STATEMENT REGARDING FEDERALLY SPONSORED RESEARCH

Not applicable.

3. BACKGROUND

Clones having optimal antibody expression characteristics are typically selected during the development of production cell lines for the generation of therapeutic monoclonal antibodies. Clones having optimal expression characteristics are expanded and frozen for future antibody production cultures. Despite the exceedingly controlled environment in which a production cell line is used, as the cells propagate and express antibody, the cell line accumulates cells that are "low expressors." As a result, the production levels of the culture as a whole decreases, and the cost of antibody production increases.

Accordingly, it is highly desirable to have a system whereby one can easily identify and select high expressors within a recombinant cell culture for future production runs. We have developed an immunoglobulin expression vector that allows simultaneous expression of membrane-bound and soluble forms of an immunoglobulin.

4. SUMMARY

Compositions and methods are described herein for the rapid identification and isolation of recombinant host cells that express immunoglobulins at a level sufficient to support manufacture scale production of therapeutic antibodies. These compositions utilize recombinant expression vectors that can exist extra-chromosomally or integrated in the chromosome to support the simultaneous expression of secreted and membrane-bound forms of an immunoglobulin.

The expression vectors are "dual display vectors" capable of directing the simultaneous expression of membrane-bound and secreted forms of an immunoglobulin. The dual display vectors typically comprise a first promoter, a first exon encoding an immunoglobulin heavy chain variable domain, a second exon encoding an immunoglobulin CH1 domain, a third exon encoding an immunoglobulin hinge domain, a fourth exon encoding an immunoglobulin CH2 domain, a fifth exon encoding a first immunoglobulin heavy chain CH3 domain and a cell surface tether domain, and a sixth exon encoding a second immunoglobulin heavy chain CH3 domain, wherein the polynucleotide sequence encoding said second immunoglobulin CH3 domain is identical to the polynucleotide sequence encoding said first immunoglobulin heavy chain CH3 domain. The vector further comprises a CH2 splice donor site located adjacent to the 3' end of the fourth exon encoding the immunoglobulin CH2 domain, a CH3-TM splice acceptor site located adjacent to the 5' end of said fifth exon encoding the immunoglobulin heavy chain CH3 domain and the cell surface tether domain, and a CH3 splice acceptor site located adjacent to the 5' end of the sixth exon encoding the second immunoglobulin heavy chain CH3 domain. The CH2 splice donor site splices alternatively to the CH3-TM splice acceptor site to form a first spliced transcript, which encodes a membrane-bound immunoglobulin, or to the CH3 splice acceptor site to form a second spliced transcript which encodes a secreted form of the same immunoglobulin, wherein the first and second spliced transcripts are simultaneously expressed in a single host cell.

In one embodiment, the CH3-TM splice acceptor site comprises the sequence SBSBGBSSSBACAG (SEQ ID NO: 1), wherein B is G, T, or C, and S is G or C.

In some embodiments, the dual display vector further comprises an IRES element and a polynucleotide encoding a heterologous marker protein. In some embodiments, the polynucleotide encoding the heterologous marker protein is downstream of the first promoter and IRES element, and the IRES element is upstream of the polynucleotide encoding the immunoglobulin heavy chain. In some embodiments, the polynucleotide encoding the IRES element is downstream of the sixth exon encoding the CH3 domain and the polynucleotide encoding the heterologous marker protein is downstream of the IRES element.

In some embodiments, the dual display vector comprises a polynucleotide encoding a cell surface tether domain which is selected from platelet derived growth factor receptor (PDGF-R) transmembrane domain, B7-1 transmembrane domain and asialoglycoprotein receptor (ASGPR) transmembrane domain. In some embodiments, the cell surface tether domain refers to a GPI signal sequence which directs anchoring of the immunoglobulin to the cell-surface via a glycosidylphosphatidylinositol (GPI) linker.

In some embodiments, the dual display vector further comprises a second promoter operatively linked to a polynucleotide sequence encoding an immunoglobulin light chain variable domain and a polynucleotide sequence encoding an immunoglobulin light chain constant domain.

In some embodiments, the dual display vector further comprises a replication origin operative in a eukaryotic cell. In some embodiments, the replication origin is an Epstein-Barr virus replication origin (OriP). In some embodiments, the dual display vector comprises a polynucleotide encoding a replication factor. In some embodiments, the polynucleotide encoding the replication factor encodes an Epstein-Barr Nuclear Antigen 1 (EBNA-1) protein.

In some embodiments, the dual display vector comprises a drug resistance gene for selection of transfected eukaryotic cells. In some embodiments, the drug resistance gene is selected from a puromycin resistance gene, a neomycin resistance gene, a hygromycin gene, a xanthine-guanine phosphoribosyltransferase gene (gpt), a zeocin resistance gene, and a blasticidin resistance gene.

In some embodiments, the dual display vector further comprises a drug resistance gene used for the selection of transformed prokaryotic cells. In some embodiments, the drug resistance gene used for selection of transformed prokaryotic cells is selected from an ampicillin resistance gene, a kanamycin resistance gene, a tetracycline resistance gene, a cefotaxime resistant gene, a carbenicillin resistance gene, an actinomycin D resistance gene, and a streptomycin resistance gene.

In some embodiments, the dual display vector further comprises a second promoter. In some embodiments, the first or second promoter is selected from a simian virus 40 (SV40) early promoter, a SV40 late promoter, a mouse mammary tumor virus promoter, a human immunodeficiency virus long terminal repeat promoter, a moloney virus promoter, an avian leukemia virus promoter, an Epstein-Barr virus immediate early promoter, a Rous sarcoma virus promoter, a human action promoter, a human hemoglobin promoter, cytomegalovirus (CMV) promoter, a human EF-1 alpha promoter, and a human muscle creatine promoter.

In some embodiments, the dual display vector comprises one or more recombinase recognition sites. In some embodiments two recombinase recognition sites flank the portion of the dual display vector comprising, in a 5' to 3' direction, a promoter, a polynucleotide encoding an immunoglobulin heavy chain variable domain, a second exon encoding an immunoglobulin CH1 domain, a third exon encoding an immunoglobulin hinge domain, a fourth exon encoding an immunoglobulin CH2 domain, a fifth exon encoding a first immunoglobulin heavy chain CH3 domain and a cell surface tether domain, and a sixth exon encoding a second immunoglobulin heavy chain CH3 domain, wherein the polynucleotide sequence encoding the second immunoglobulin CH3 domain is identical to the polynucleotide sequence encoding the first immunoglobulin heavy chain CH3 domain. The dual expression vector further comprises a CH2 splice donor site located adjacent to the 3' end of the fourth exon encoding the immunoglobulin CH2, a CH3-TM splice acceptor site located adjacent to the 5' end of the fifth exon encoding the immunoglobulin heavy chain CH3 domain and a cell surface tether domain, and a CH3 splice acceptor site located adjacent to the 5' end of the sixth exon encoding the second immunoglobulin heavy chain CH3 domain, wherein the CH2 splice donor site splices alternatively to the CH3-TM splice acceptor site to form a first spliced transcript for producing a membrane-bound immunoglobulin, or to the CH3 splice acceptor site to form a second spliced transcript for producing a secreted form of the same immunoglobulin.

In some embodiments, the portion of the dual display vector flanked by two recombinase recognition sites further comprises a polynucleotide encoding an immunoglobulin light chain. In some embodiments, eukaryotic host cells comprise dual display vector polynucleotide sequences which are flanked by recombinase recognition sites. In some embodiments, the polynucleotide sequences which are flanked by recombinase recognition sites are integrated into the recombinant cell genomic DNA. In some embodiments, the recombinase recognition site is recognized by a recombinase selected from the Flp recombinase, Cre recombinase, Int recombinase, Sin recombinase and Hin recombinase.

In some embodiments, dual display vector polynucleotide sequences encoding variable domains are generated from an antibody-producing cell isolated from any animal capable of producing antibodies upon immunization. In this embodiment, the target antigen can be used to immunize animals including but not limited to chicken, rabbit, llama, sheep, mouse, rat, hamster, non-human primate, or human. In some embodiments, variable domains are generated from naturally occurring antibody-producing cells that recognize the target antigen of interest and that are isolated from the animal.

In some embodiments, a eukaryotic cell is transfected with the dual display vector. Eukaryotic cells suitable for use in the methods described herein are selected from 293-HEK, HeLa, Jurkat, Raji, Daudi, COS, NS0, Per.C6, SP2.0, and CV-1 cells.

Transfected cells expressing cell surface-bound immunoglobulins can be identified by contacting the transfected cell with a target antigen, and selecting transfected cells that specifically bind the target antigen. In some embodiments, immunoglobulins comprising the heavy and light chain variable and constant domains displayed on the surface of mammalian cells are screened for antigen binding to a target antigen using magnetic bead and/or fluorescence-activated cell sorting. In some embodiments, the levels of secreted antibody is assayed using CellSpot™ or ClonePix FL.

Several methods can be used to identify CH3-TM splice acceptor site sequences which splice with a CH2 splice donor site with decreased efficiency as compared to splicing of the CH3 splice acceptor site to the CH2 splice donor site. In some embodiments, this method comprises transfecting eukaryotic cells with the dual expression vector to produce transfected eukaryotic cells, incubating the transfected cells under conditions sufficient for expressing immunoglobulin on the surface of the transfected cells, contacting the transfected cells with a target antigen, and selecting transfected cells based on the level of surface-bound immunoglobulin expressed by the cell.

5. BRIEF DESCRIPTION OF THE FIGURES

FIG. 1 depicts an embodiment of the dual display vector.

FIGS. 2A-2B depict FACS analysis of cells transfected with various embodiments of the dual display vector. Cells transfected with: A) dual display vector pYA400; B) vector pYA401.

FIG. 4 depicts CH3-TM splice acceptor site sequences present in dual display vectors that were shown by FACS analysis to express decreased levels of surface-bound immunoglobulins. FIG. 4 discloses the sequences in the "Sequence" column as SEQ ID NOS 4 and 42-55 and the sequences in the "Base to Base Alignment" column as SEQ ID NOS 4, 1, and 42-55, respectively, in order of appearance.

FIG. 5 depicts the pYA400 vector.

6. DETAILED DESCRIPTION

Figure 1:
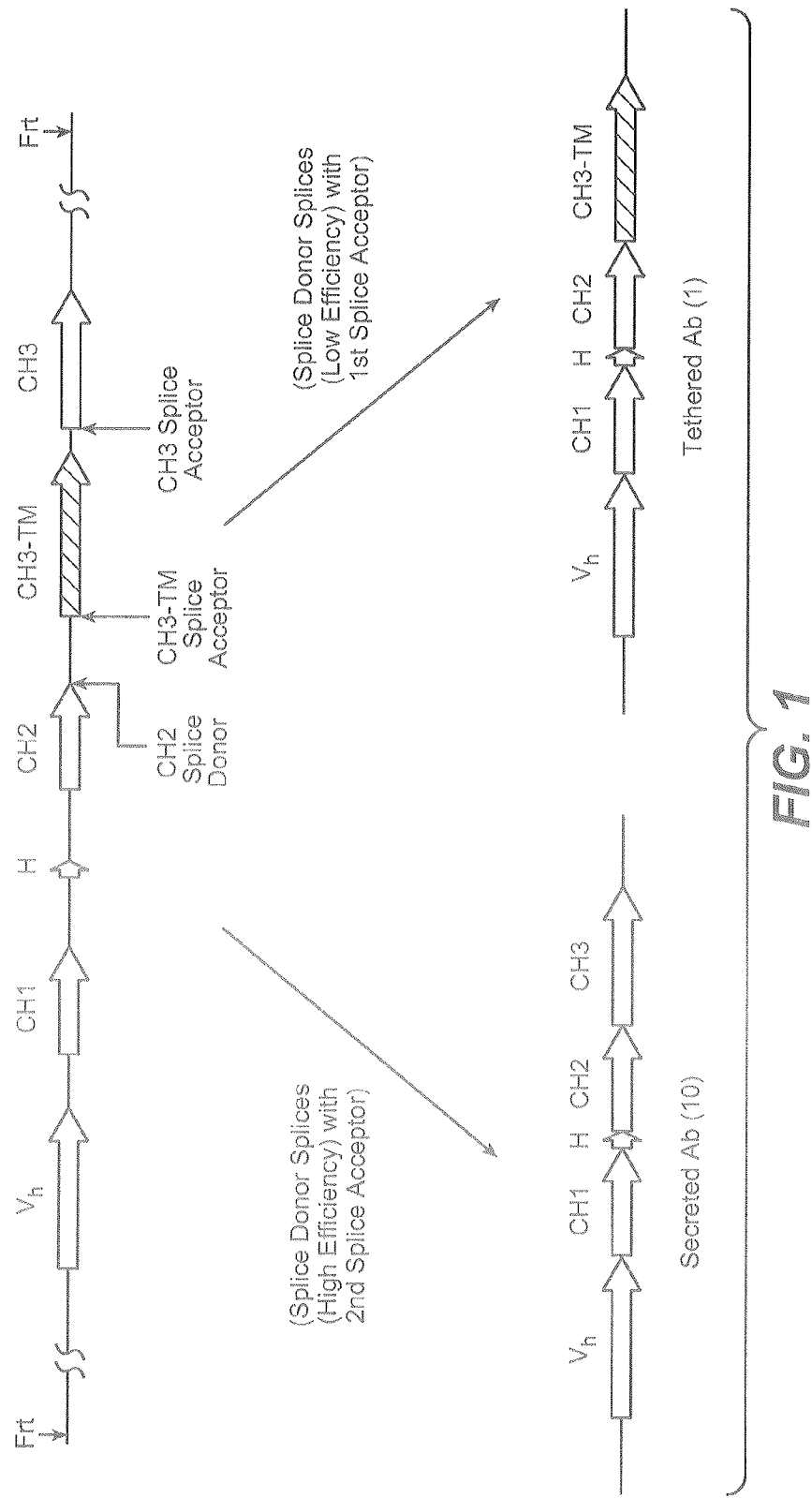

Compositions and methods that allow the simultaneous expression of secreted and membrane-bound forms of an immunoglobulin within a single host cell are described herein. Host cells are transfected with an expression vector which directs the generation of two alternative mature mRNA transcripts in a single transfected host cell. Translation of the two alternate transcripts results in a membrane-bound and secreted form of an immunoglobulin in that cell.

An advantage associated with expression vector described herein is the ability to rapidly select transfected cells expressing relatively high levels of an immunoglobulin on the surface of the cell, and directly use these cells to express high levels of the secreted form of the immunoglobulin.

6.2 Definitions

It is to be understood that both the foregoing general description and the following detailed description are exemplary and explanatory only and are not restrictive of the compositions and methods described herein. In this application, the use of the singular includes the plural unless specifically stated otherwise. Also, the use of "or" means "and/or" unless state otherwise. Similarly, "comprise," "comprises," "comprising," "include," "includes" and "including" are not intended to be limiting.

As used herein, the following terms and phrases are intended to have the following meanings:

A "cell surface tether domain" as used herein, refers to an amino acid sequence that confers the ability of a polypeptide to be associated with a host cell membrane, but which is not naturally present in the protein of interest. As described herein, cell surface tether domains include, for example, transmembrane domains or glycosidylphosphatidylinositol (GPI) signal sequences. GPI signal sequences can be recognized as described in Udenfriend and Kodukula (1995), Methods Enzymol. 250:571-582. It is understood that GPI signal sequences specify a processing event in the cell that results in cleavage and removal of the GPI signal domain and covalent attachment of a GPI anchor to the new C-terminus of the protein. In the case of DAF, the last about 30-50 residues of DAF contain a signal that directs a processing event in cells in which the last about 28 residues are proteolytically removed and replaced with a hydrophobic glycolipid (GPI) that acts as a membrane anchor. Transmembrane domains can be predicted as described by Sonnhamer et al. (1998), Proc. of ISMB 6:175-182. Transmembrane domains and GPI anchor sequences that can be recognized as described above are membrane association sequences as meant herein. A protein comprising a membrane association sequence may, in many cases, be associated with the cell surface, particularly if the protein also comprises a signal sequence in its precursor form (see discussion of "signal sequence" below). Association of a protein with a cell surface can be determined by fluorescence activated cell sorting (FACS) analysis using non-permeabilized cells that express the protein. FACS is described in, e.g., Current Protocols in Cytometry, Robinson et al., eds., John Wiley & Sons (2004); Edidin (1989), Methods in Cell Biology 29:87-102.

The term "expression vector" as used herein, refers to a non-naturally occurring DNA molecule that comprises a promoter operably linked to a polynucleotide encoding a recombinant protein or a peptide. The expression vector comprises at least one replication origin (also referred to as "origin of replication"). The replication origin confers the ability to replicate in a host and may be viral, eukaryotic, or prokaryotic. The expression vector may be used to stably or transiently transfect a eukaryotic cell line or may be used in transformation of a prokaryotic cell. The expression vector may exist extra-chromosomally in a transient transfectant. In a stable transfectant, the expression vector may be propagated as an episomal vector or may be integrated into the host cell chromosome. The expression vector of the present invention may further comprise additional elements, for example, IRES elements, exons, introns, and a polyA signal sequence, and one or more selectable marker genes to facilitate recognition of prokaryotic or eukaryotic transfectants.

A "signal peptide" in the present invention is a hydrophobic sequence that mediates insertion of the protein through the membrane bounding the ER. Type I transmembrane proteins also comprise signal sequences. "Signal sequences," as meant herein are amino-terminal hydrophobic sequences which are usually enzymatically removed following the insertion of part or all of the protein through the ER membrane into the lumen of the ER. Thus, it is known in the art that a signal precursor form of a sequence can be present as part of a precursor form of a protein, but will generally be absent from the mature form of the protein. When a protein is said to comprise a signal sequence, it is to be understood that, although a precursor form of the protein does contain the signal sequence, a mature form of the protein will likely not contain the signal sequence. Examples of signal peptides or sequences that are functional in mammalian host cells include the following: the signal sequence for interleukin-7 (IL-7) described in U.S. Pat. No. 4,965,195; the signal sequence for interleukin-2 receptor described in Cosman et al. ((1984), Nature 312:768); the interleukin-4 receptor signal peptide described in EP Patent No. 0 367 566; the type I interleukin-1 receptor signal sequence described in U.S. Pat. No. 4,968, 607; the type II interleukin-1 receptor signal peptide described in EP Patent No. 0 460 846; the signal sequence of human IgK (which is METDTLLLWVLLLWVPGSTG (SEQ ID NO: 2)); and the signal sequence of human growth hormone (MATGSRTSLLLAFGLLCLPWLQEGSA (SEQ ID NO: 3)). Many other signal sequences are known in the art. In the present invention, the signal peptide may be the naturally occurring signal peptide for a protein of interest or it may be a heterologous signal peptide.

The term "CH2 splice donor site" in the present invention refers to a splice donor site that is adjacent and downstream to the 3' end of the exon which encodes the immunoglobulin heavy chain CH2 domain. The CH2 splice donor site will splice to the CH3-TM splice acceptor site or to the CH3 splice acceptor site.

The "CH3-TM splice acceptor site" is the splice site sequence adjacent to and upstream of the exon encoding the CH3-TM domain. The "CH3 splice acceptor site" is the splice site sequence adjacent to and upstream of the exon encoding the CH3-TM domain.

Promoters (and other genetic regulatory elements) are typically "operably linked" to coding sequences. "Operably linked" refers to a juxtaposition of two or more components, wherein the components so described are in a relationship permitting them to function in their intended manner. For example, a promoter and/or enhancer is operably linked to a coding sequence if it acts in cis to control or modulate the transcription of the linked sequence. Generally, but not necessarily, the DNA sequences that are "operably linked" are contiguous and, where necessary to join two protein coding regions or in the case of a secretory leader, contiguous and in reading frame. However, although an operably linked promoter is generally located upstream of the coding sequence, it is not necessarily contiguous with it. A polyadenylation site is operably linked to a coding sequence if it is located at the downstream end of the coding sequence such that transcription proceeds through the coding sequence into the polyadenylation sequence. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

The term "antigen" as used herein is defined as a molecule that provokes an immune response. This immune response may involve either antibody production, or the activation of specific immunologically-competent cells, or both. Antigens may be soluble substances, such as toxins and foreign proteins, or particulates, such as bacteria and tissue cells; however, only the portion of the protein or polysaccharide molecule known as the antigenic determinant (epitopes) combines with antibody or a specific receptor on a lymphocyte. Accordingly, any macromolecule, including virtually all proteins or peptides, can serve as an antigen.

The term "cell surface antigen" is a cell-associated component that can behave as an antigen without disrupting the integrity of the membrane of the cell expressing the antigen.

The term "antibody" or "immunoglobulin" as used herein refers to a protein consisting of one or more polypeptides substantially encoded by immunoglobulin genes. The recognized immunoglobulin genes include the kappa, lambda, alpha, gamma (IgG1, IgG2, IgG3, IgG4), delta, epsilon and mu constant domain genes, as well as the myriad immunoglobulin variable (V) domain genes (as indicated below, there are V genes for both H-heavy- and L-light-chains).

A "chimeric antibody" as used herein is an antibody molecule in which (a) the constant region or domain, or a portion thereof, is altered, replaced, or exchanged so that the antigen binding site (variable region) is linked to a constant region of a different or altered class, and/or species, or an entirely different molecule which confers new properties to the chimeric antibody, e.g., an enzyme, toxin, hormone, growth factor, drug, effector function, chemoattractant, immune modulator, etc.; or (b) the variable region, or a portion thereof, is altered, replaced, or exchanged with a variable region having a different or altered antigen specificity.

The term "humanized antibody" or "humanized immunoglobulin" as used herein refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,530,101; 5,585,089; 5,693,762; and 6,180,370; these and the other U.S. patents/patent applications are incorporated by reference in their entirety.

The term "epitope" as used herein refers to any portion (determinant) of a protein that is capable of eliciting an immune response and being specifically bound by an antibody. Epitope determinants usually consist of active surface groupings of molecules such as amino acids, and usually have specific three-dimensional structural characteristics, as well as specific charge characteristics. Two antibodies are said to bind to substantially the same epitope of a protein (or the overlapping epitope of a protein) if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. An example of a competition assay for use herein is described in U.S. Patent Publication No. 2005/0025763, incorporated herein by reference in its entirety.

"Nucleic acid" or "oligonucleotide" or "polynucleotide" or grammatical equivalents as used herein means at least two nucleotides covalently linked together. Oligonucleotides are typically from about 5, 6, 7, 8, 9, 10, 12, 15, 25, 30, 40, 50, or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have at least one different linkage, e.g., phosphoramidate, phosphorothioate, phosphorodithioate, or O-methylphosphoroamidite linkages (see Eckstein (1992) Oligonucleotides and Analogues: A Practical Approach Oxford Univ. Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7 of Sanghvi and Cook (eds. 1994) Carbohydrate Modifications in Antisense Research ACS Symposium Series 580. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The depiction of a single strand also defines the sequence of the complementary strand; thus the sequences described herein also provide the complement of the sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

The term "polylinker" as used herein is a nucleic acid sequence that comprises a series of two or more different restriction endonuclease recognition sequences closely spaced to one another (i.e. less than 10 nucleotides between each site).

The terms "polypeptide," "peptide," and "protein," are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" as used herein refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain some basic chemical structure as a naturally occurring amino acid Amino acid mimetic refers to a chemical compound that has a structure that is different from the general chemical structure of an amino acid, but that functions similarly to another amino acid.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The term "recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed, or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant.

The term "recombinant protein" as used herein, is a protein made using recombinant techniques, e.g., through the expression of a recombinant nucleic acid as depicted above. A recombinant protein is distinguished from naturally occurring protein by at least one or more characteristics. The protein may be isolated or purified away from some or most of the proteins and compounds with which it is normally associated in its wild type host, and thus may be substantially pure. An isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a recombinant protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

6.3 Detailed Description

6.3.1 Dual Display Vector

Dual display vectors capable of directing the simultaneous expression of a membrane-bound and secreted form of an immunoglobulin are described herein. "Simultaneous expression" refers to the generation of two mRNA splice variants in a single host cell. If first and second spliced transcripts are present and co-expressed in a single host cell, this means that a single expression vector has led to the transcription of a single species of primary transcript, followed by differential splicing such that two different mature mRNAs are generated from the single primary transcript species, and each mature mRNA is used as a template for translation within the host cell, such that proteins are generated from each, leading to the production of two different proteins encoded by the same expression vector. These two different proteins typically differ in the presence or absence of a cell surface tether domain.

In some embodiments, the dual display vector comprises a gene encoding an immunoglobulin heavy chain constant domain having naturally-occurring exons, introns, splice donor sites, and splice acceptor sites. In some embodiments, the polynucleotide encoding an immunoglobulin heavy chain constant domain comprises, in a 5' to 3' direction, an intron (intron 1), an exon encoding a CH1 domain, an intron (intron 2), an exon encoding a hinge domain, an intron (intron 3), an exon encoding a CH2 domain, an intron (intron 4), and an exon encoding a CH3 domain. In some embodiments, a polynucleotide encoding a heavy chain variable domain is located upstream of the polynucleotide encoding the heavy chain constant domain. In some embodiments, a first promoter is operably linked to the polynucleotides encoding the immunoglobulin heavy chain variable and constant domains. In some embodiments, a second promoter and a polynucleotide encoding an immunoglobulin light chain, comprising the variable and constant domains, is located upstream of the first promoter of the dual display vector. In some embodiments, a second promoter and a polynucleotide encoding an immunoglobulin light chain, comprising the variable and constant domains, is located downstream of the sixth exon of the dual display vector. In some embodiments, the dual display vector further comprises a poly A signal sequence within intron 4.

The dual display vectors can further comprise an additional intron (intron 4') which is a duplicate of intron 4, and an additional exon which encodes a duplicate copy of the CH3 domain of the immunoglobulin heavy chain constant domain. The additional exon further comprises a polynucleotide encoding a cell surface tether domain that is ligated to the 3' end of the CH3 coding sequence, and is referred to herein as the "CH3-TM" exon. Typically, the intron 4' and CH3-TM exon sequences are located between the CH2 exon and intron 4. Cell surface tether domains suitable for use herein include, but are not limited to, platelet derived growth factor receptor (PDGF-R) transmembrane domain, B7-1 transmembrane domain, asialoglycoprotein receptor (ASGPR), and a glycosidylphosphatidylinositol (GPI) linker.

A gene encoding the immunoglobulin heavy chain constant domain can be generated and subcloned into an expression vector by methods well known in the art. See, e.g., Co et al. (J. Immunology, 148:1149, 1992). Heavy chain constant domains suitable for use in the vectors described herein include, but are not limited to, gamma-1, gamma-2, gamma-3, gamma-4, mu, delta, epsilon, alpha-1, or alpha-2 heavy chain constant domain, from a variety of species.

An exemplary embodiment of the dual display vector as described above is shown in FIG. 1, in which the immunoglobulin heavy chain constant domain is encoded by individual exons. As illustrated in FIG. 1, transcriptionally the vector comprises from a 5' to 3' direction, a first exon encoding an immunoglobulin heavy chain variable domain (Vh), a second exon encoding an immunoglobulin CH1 domain (CH1), a third exon encoding an immunoglobulin hinge domain (H), a fourth exon encoding an immunoglobulin CH2 domain (CH2), a fifth exon encoding a first immunoglobulin heavy chain CH3 domain and a cell surface tether domain (CH3-TM), and a sixth exon encoding a second immunoglobulin heavy chain CH3 domain (CH3). The polynucleotide sequence encoding the second immunoglobulin CH3 domain is identical to the polynucleotide sequence encoding the first immunoglobulin heavy chain CH3 domain. The CH2 splice donor site is located adjacent to the 3' end of the fourth exon encoding the immunoglobulin CH2 domain. The CH3-TM splice acceptor site is located adjacent to the 5' end of the fifth exon encoding the immunoglobulin heavy chain CH3 domain and a cell surface tether domain. FIG. 1 also illustrates the two forms of mature mRNA transcripts generated by splicing of the CH2 splice donor site to the CH3-TM splice acceptor site or to the CH3 splice acceptor site.

6.3.2 Splice Donor and Acceptor Site Sequences

The dual display vector comprises splice donor and splice acceptor sites at the intron-exon borders of the polynucleotide sequence encoding the immunoglobulin heavy chain. The "CH2 splice donor site" is the splice site sequence that is typically located adjacent to the 3' end of the exon encoding the CH2 domain. The "CH3-TM splice acceptor site" is the splice site sequence that is typically located adjacent to the 5' end of the CH3-TM exon. The "CH3 splice acceptor site" is the splice site sequence that is typically located adjacent to the 5' end of the CH3 exon. In some embodiments, the CH2 splice donor site splices to the CH3-TM splice acceptor site or to the CH3 splice acceptor site. This results in the primary mRNA transcript being spliced to form two mature mRNA transcripts: one that encodes a membrane-bound immunoglobulin and one that encodes a secreted form of the same immunoglobulin.

Methods known to those of skill in the art can be used to identify exons, introns, splice donor sites, and splice acceptor sites within genomic DNA sequences. For example, one may obtain the cDNA sequence encoding the protein of interest and use a pairwise alignment program such as FASTA to align the cDNA sequence to the genomic DNA sequence. Resulting gaps in the cDNA sequence will denote the location of intronic regions in the genomic DNA.

Evaluation of DNA or RNA sequences for the presence of one or more consensus or near consensus splice sites can be performed manually or by using a computer algorithm. For example, a program such as MacVector™ or VectorNTI can be employed to search nucleotide sequences for specified base patterns (e.g., the MacVector™ program). The latter approach is preferred for large DNAs or RNAs, because it allows for easy implementation of multiple search parameters.

Methods of determining splice site sequences at the intron-exon borders are known to those skilled in the art. By way of example, a consensus or near consensus splice site can be identified within a DNA, or its corresponding RNA transcript, by evaluating the nucleotide sequence of the DNA for the presence of a sequence which is identical or highly homologous to either a splice acceptor site or a splice donor site. Such consensus and near consensus sites can be located within any portion of a given DNA (e.g., a gene), including the coding region of the DNA and any 3' and 5' untranslated regions.

In some embodiments, consensus and near consensus splice acceptor sites can be identified by analyzing a DNA (or corresponding RNA) sequence for the presence of one or more nucleotide sequences that include an AG base pair and are identical to, or at least about 50% homologous, more preferably at least about 60-70% sequence homologous, to the sequence: (T/C)≧8 N(C/T)AGG. In some embodiments, the nucleotide sequence is followed upstream, typically by about 40 bases, by a nucleotide sequence which is identical to or highly homologous (e.g., at least about 50%-95% homologous) to a branch consensus sequence comprising the following bases: (C/T)N(C/T)T(A/G)A(C/T), wherein N is any nucleotide. By way of example, in studies described in U.S. Pat. No. 6,642,028 (the content of which are incorporated herein by reference in its entirety), consensus and near consensus splice acceptor sites were selected for engineering within a gene encoding Factor VIII using the following criteria: the consensus or near consensus site (a) contained an AG pair, and (b) contained no more than three mismatches to a 3' consensus site.

In some embodiments, consensus and near consensus splice donor sites are identified by analyzing, a DNA (or corresponding RNA) sequence for the presence of one or more nucleotide sequences which contain a GT base pair, and which are identical to or at least about 50% homologous, more preferably at least about 60-70% homologous, to the sequence: (A/C)AGGT(A/G)AGT. In studies described in U.S. Pat. No. 6,642,028, consensus and near consensus splice acceptor sites were selected for engineering within a gene encoding Factor VIII using the following criteria: the consensus or near consensus site (a) contained a GT pair, and (b) contained no more than four mismatches to a 5' consensus site, provided that if it contained four mismatches, they were located consecutively in a row.

6.3.3 mRNA Splicing

In the dual display vector described herein, the CH2 splice donor site can splice to the CH3-TM splice acceptor site or to the CH3 splice acceptor site. Upon post-transcription splicing of the primary mRNA transcript, splicing of the CH2 splice donor site to the CH3-TM splice acceptor site results in expression of the membrane-bound immunoglobulin. Alternatively, splicing of the CH2 splice donor site to the CH3 splice acceptor site results in expression of the secreted immunoglobulin.

In some embodiments, the CH2 splice donor has the sequence GTGGGA, and the CH3-TM and CH3 splice acceptor sites have the sequence CTCTGTCCCTACAG (SEQ ID NO: 4). In some embodiments, the CH3-TM splice acceptor site has the sequence SBSBGBSSSBACAG (SEQ ID NO: 1), wherein B is either G, T, or C and S is either G or C.

In some embodiments, the CH3-TM splice acceptor site has been mutated such that the CH2 splice donor site splices more efficiently with the CH3 splice acceptor site than it does with the CH3-TM splice acceptor site. Accordingly, depending on the nature of the mutated CH3-TM splice acceptor sites, varying ratios of membrane-bound to secreted immunoglobulin can be produced. For example, a dual display vector comprising a mutated CH3-TM splice acceptor site generates a higher ratio of secreted to membrane bound. The ratio of secreted to membrane bound immunoglobulin will depend on the effect the mutation(s) had on the ability of the CH2 splice donor site to splice with the CH3-TM splice acceptor site. The more severe the effect, the greater the ratio of secreted to membrane-bound immunoglobulin produced.

In some embodiments, the transfected host cell comprises a dual display vector of the present invention and expresses the secreted form of the immunoglobulin relative to the membrane-bound form at a ratio of about 100:1 to about 1:100, about 90:1 to about 1:90, about 75:1 to about 1:75, about 50:1 to about 1:50, 20:1 to about 1:20, about 15:1 to about 1:15, about 12:1 to about 1:12, about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2, or about 1:1

6.3.4 Cell Surface Tether Domains

In some embodiments, the dual display vector comprises a polynucleotide encoding a cell surface tether domain. The cell surface tether domains used to display tetrameric immunoglobulin molecules on the cell surface can be any peptide domain that causes the immunoglobulin to which the cell surface tether domain is fused to be anchored to the cell surface of the transfected host cell. Essentially any transmembrane domain is compatible with vectors described herein. Transmembrane domains include, but are not limited to: a member of the tumor necrosis factor receptor superfamily, CD30, platelet derived growth factor receptor (PDGFR, e.g. amino acids 514-562 of human PDGFR; Chestnut et al. 1996 J Immunological Methods 193:17-27; also see Gronwald et al. 1988 PNAS 85:3435); nerve growth factor receptor, Murine B7-1 (Freeman et al. 1991 J Exp Med 174:625-631), asialoglycoprotein receptor H1 subunit (ASGPR; Speiss et al. 1985 J Biol Chem 260:1979-1982), CD27, CD40, CD120a, CD120b, CD80 (Freeman et al. 1989 J Immunol 143:2714-22) lymphotoxin beta receptor, galactosyltransferase (E.G. GenBank accession number AF155582), sialyltransferase (E.G. GenBank accession number NM-003032), aspartyl transferase 1 (Asp1; e.g. GenBank accession number AF200342), aspartyl transferase 2 (Asp2; e.g. GenBank accession number NM-012104), syntaxin 6 (e.g. GenBank accession number NM-005819), ubiquitin, dopamine receptor, insulin B chain, acetylglucosaminyl transferase (e.g. GenBank accession number NM-002406), APP (e.g. GenBank accession number A33292), a G-protein coupled receptor, thrombomodulin (Suzuki et al. 1987 EMBO J 6, 1891) and TRAIL receptor.

In some embodiments, the transmembrane domain is from a human protein. As will be appreciated by a person skilled in the art, all or part of a transmembrane domain from a protein may be utilized.

In some embodiments, a cell surface displayed antibody or fragment thereof of the current invention comprises the transmembrane domain of human platelet derived growth factor receptor (PDGF-R) having an amino acid sequence of AVGQDTQEVIVVPHSLPFKVVVISAILA-LVVLTIISLIILIMLWQKKPR (SEQ ID NO: 5), fused to the C-terminus of the CH3 domain of the immunoglobulin heavy chain protein. In some embodiments, a cell surface displayed antibody or fragment thereof of the current invention comprises the transmembrane domain of the B7 (CD80) protein having an amino acid sequence of KPPEDPPDSKNTLVLF-GAGFGAVITVVVIVVIIKCFCKHRSCFR-RNEASRETNNSLTFGPEEALAEQTVFL (SEQ ID NO: 6).

In some embodiments, the cell surface tether domain may be a GPI (glycosidylphosphatidylinositol) signal domain that specifies a processing event in the cell that results in cleavage and removal of the 29-37 residue GPI signal domain, and covalent attachment of a GPI anchor to the new C-terminus of the protein. It will be understood that "GPI-linked" when used in reference to expressed proteins of interest refers to the post-translationally modified fusion. For example, an immunoglobulin that is ordinarily secreted will be produced in the transfected cell culture as a C-terminal fusion of the preprotein with the GPI signal domain. Rather than being secreted, this fusion will become GPI-linked during processing and will be transported to the cell membrane and remain lodged there by virtue of the GPI anchor.

Several proteins are known that contain the C-terminal domains substituted with phospholipids anchors. Such proteins include Thy-1 (Low et al., Nature (London) 318:62 [1985] and Tse et al., Science 230:1003 [1985]), the variant surface glycoproteins (VSGs) of African trypanosomes (Ferguson et al., J. Biol. Chem. 260:14547 [1985]), acetylcholinesterase (Futerman et al., Biochem. J. 226:369 [1985]), 5' nucleotidase (Low et al., Biochim. Biophys. Acta 508:565 [1978]), and DAF (Davitz et al., J. Exp. Med. 163:1150 [1986] and, Medof et al., Biochemistry 25:6740 [1986]). Attachment of the DAF anchor, which contains glycosylated phosphatidylinositol (PI) and ethanolamine, apparently occurs following proteolytic removal of 17-31 C-terminal residues from mDAF (Low, M. G. Biochem J., 244:1-13 [1987] and Cross, G. A. M., Cell 48:179-181 [1987]).

One skilled in the art can adapt the method performed in Chou et al. to optimize or screen different transmembrane domains and/or GPI-anchor domains for use in compositions and methods described herein.

6.3.5 Immunoglobulin Domains

The dual display vectors described herein are typically used to display intact antibodies, although antibody fragments, e.g., Fc, Fab', F(ab)'2, and single chain Fv, can also be displayed. Generally, each light chain and each heavy chain is encoded in a separate transcriptional unit, or gene. The recognized immunoglobulin genes include the kappa and lambda light chain constant region genes, the alpha, gamma (IgG1, IgG2, IgG3, IgG4), delta, epsilon and mu heavy chain constant region genes, and immunoglobulin variable region genes. The polynucleotides used in the mammalian display vectors can encode any of the recognized immunoglobulin genes, as well as immunoglobulin variable V region genes Examples of suitable sources for immunoglobulin genes include, but are not limited to, humans, primates, rodents (e.g., rat, mouse, hamster, guinea pig), turkey, quail, trout, shark, camel and non-rodents, such as sheep, chicken, llama and rabbit. In addition to immunoglobulins obtained from various organisms, variant forms of known antibodies can be used, including humanized, chimeric and monoclonal antibodies. Methods of obtaining polynucleotide encoding immunoglobulin variable domains are well known in the art and include PCR-amplification and sub-cloning.

In some embodiments, polynucleotide sequences encoding heavy and light chain constant domains are cloned from mRNA expressed by antibody-producing cells. In other embodiments, polynucleotide sequences encoding heavy and light chain constant domains are cloned from genomic DNA.

6.3.6 Internal Ribosome Entry Sites (IRES Elements)

IRES sequences can be used to produce multicistronic transcripts which include coding sequences for multiple proteins. These coding sequences may encode the same protein, or different proteins e.g., the heavy and light chains of an antibody. By including coding sequences for multiple proteins in a single transcript, equivalent expression levels for the proteins can be obtained. IRES sequences can be incorporated in expression vectors to produce subunits of a molecular complex from a single transcriptional unit, or to readily incorporate selectable and/or scorable reporters into exchangeable segments without creating fusion proteins or the use of additional regulatory elements to control expression of the second gene.

Examples include those IRES elements from poliovirus Type I, the 5'UTR of encephalomyocarditis virus (ECMV), of "Thelier's murine encephalomyelitis virus (TMEV) of "foot and mouth disease virus" (FMDV) of "bovine enterovirus (BEV), of "coxsackie B virus" (CBV), or of "human rhinovirus" (HRV), or the "human immunoglobulin heavy chain binding protein" (BIP) 5'UTR, the *Drosophila* antennapediae 5'UTR or the *Drosophila* ultrabithorax 5'UTR, or genetic hybrids or fragments from the above-listed sequences. IRES sequences are described in Kim, et al., 1992, Molecular and Cellular Biology 12:3636-3.643 and McBratney, et al., 1993, Current Opinion in Cell Biology 5:961-965.

6.3.7 Self-Replicating Vector Elements

The dual display vectors can be linear or circular, single or double-stranded. The vectors are generally within the size range of 1 kb-100 kb, but typically are between 1 to 10 kb, 10 to 20 kb, 20 to 30 kb, 30 to 40 kb, 40 to 50 kb, 50 to 60 kb, 60 to 70 kb, 70 to 80 kb, 80 to 90 kb, and 90 to 100 kb.

The dual display vectors for use in the compositions and methods described herein typically comprise a portion of a virus genomic DNA or cDNA that encodes an origin of replication (ori) required for the vectors to be self-replicating. In addition, the vectors can contain one or more genes encoding viral proteins that are required for replication, i.e., replication factors. In some embodiments, the replication factors can be expressed in trans on another vector in the cell or from the genomic DNA of the host cell. In some embodiments, the replication factors can be encoded by a viral genome that is maintained in a episomal state in the host cell.

In some embodiments, the viral origin of replication is the oriP of Epstein-Barr virus (EBV) and the replication protein factor is the trans-acting EBNA-1 protein or a variant thereof. EBNA-1 can be expressed on the episomal display vector carrying oriP, on another vector present in the cell, or from an EBNA-1 gene in the genomic DNA of the host cell. The oriP from EBV is described in Yates et al., 1985, Nature, 313, 812-815, Sugden et al., 1985, Mol Cell Biol, 5, 410-413, Margolskee et al., 1988, Mol Cell Biol, 8, 2837-2847, and in Chittenden et al., 1989 J Virol, 63, 3016-3025.

In some embodiments, the dual display vectors comprise the replication functions of the papilloma family of viruses, including but not limited to Bovine Papilloma Virus (BPV) and Human Papilloma Virus (HPVs). BPV and HPVs persist as stably maintained plasmids in mammalian cells. Two trans-acting factors encoded by BPV and HPV, namely E1 and E2, or variants thereof are sufficient for supporting replication in many mammalian cells (Ustav et al., 1991, EMBO J, 10, 449-457, Ustav et al., 1991, EMBO J, 10, 4231-4329, Ustav et al., 1993, Proc Natl Acad Sci USA, 90, 898-902, Piirsoo et al., 1996, EMBO J, 15, 1-11, and PCT Publication WO 94/12629.

In some embodiments, the dual display vectors can be derived from a human papovavirus BK genomic DNA molecule. For example, the BK viral genome can be digested with restriction endonucleases EcoRI and BamHI to produce a fragment that contains the BK viral origin of replication sequences that can confer stable maintenance on vectors (see, for example, De Benedetti and Rhoads, 1991, Nucleic Acids Res, 19:1925-1931), as can a 3.2 kb fragment of the BK virus (Cooper and Miron, 1993, Human Gene Therapy, 4:557-566).

For propagation and/or use in prokaryotic host cells, the vectors also include a prokaryotic origin of replication. Prokaryotic origins of replication suitable for use in the compositions and methods described herein include, but are not limited to, pUC, Col E1, p15A, Ori S, lambda, and/or P1.

6.3.8 Promoters

Typically, the dual display vectors include one or more promoters and/or enhancers capable of directing the expression of the polynucleotide sequences in the various cell types used in the compositions and methods described herein. The promoters can be constitutive, tissue-specific, inducible, and/or useful under the appropriate conditions to direct expression of the introduced polynucleotide sequence(s). The promoters can be heterologous or endogenous. Promoters suitable for use in compositions and methods described herein include, but are not limited to, the cytomegalovirus (CMV) promoter, the simian virus 40 (SV40) early or late promoters, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, the actin promoter, the myosin promoter, the hemoglobin promoter, the EF-1 alpha promoter, and/or the muscle creatine promoter.

6.3.9 Selectable Markers

The inclusion of one or more polynucleotides encoding selectable markers aids in the identification of transformants. Typical selection genes encode proteins that (a) confer resistance to antibiotics or other toxins, (b) complement auxotrophic deficiencies, or (c) supply critical nutrients not available from complex media, e.g., the gene encoding D-alanine racemase for Bacilli.

Exemplary selection systems include, but are not limited to, the herpes simplex virus thymidine kinase (Wigler, et al., 1977, Cell 11:223-232), hypoxanthine-guanine phosphoribosyltransferase (Szybalska & Szybalski, 1962, Proc. Natl. Acad. Sci. USA 48:2026-2034), and adenine phosphoribosyltransferase (Lowy et al., 1980, Cell 22:817-823) genes can be employed in tk-, hgprt- or aprt cells, respectively. Also, antimetabolite resistance can be used as the basis of selection for dhfr, which confers resistance to methotrexate (Wigler et al., 1980, Proc. Natl. Acad. Sci. USA 77:3567-3570; O'Hare et al., 1981, Proc. Natl. Acad. Sci. USA 78:1527-1531); gpt, which confers resistance to mycophenolic acid (Mulligan & Berg, 1981, Proc. Natl. Acad. Sci. USA 78:2072-2076); neo, which confers resistance to the aminoglycoside G-418 (Colberre-Garapin et al., 1981, J. Mol. Biol. 150:1-14); hygro, which confers resistance to hygromycin genes (Santerre, et al., 1984, Gene 30:147-156); neomycin resistance (neo), hypoxanthine phosphoribosyl transferase (HPRT), puromycin (puro), dihydro-orotase glutamine synthetase (GS), carbamyl phosphate synthase (CAD), multidrug resistance 1 (mdr1), aspartate transcarbamylase, adenosine deaminase (ada), and blast, which confers resistance to the antibiotic blasticidin.

Additional selectable genes that can be used in the compositions and methods described herein also include, trpB, which allows cells to utilize indole in place of tryptophan; hisD, which allows cells to utilize histinol in place of histidine (Hartman & Mulligan, 1988, Proc. Natl. Acad. Sci. USA 85:8047-8051); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.). The use of visible reporters has gained popularity with such reporters as anthocyanins, glucuronidase and its substrate GUS, luciferase and its substrate luciferin. Green fluorescent proteins (GFP) (Clontech, Palo Alto, Calif.) and related derivatives such as Yellow Fluorescent Protein (YFP) and Emerald Green Fluorescent Protein (EmGFP) (Invitrogen Corporation, Carlsbad, Calif.) can be used as both selectable reporters (see, e.g., Chalfie, M. et al., 1994, Science, 263:802-805) and homeostatic scorable reporters (see, e.g., Rhodes, C. A. et al., 1995, Methods Mol. Biol., 55:121-131).

In other embodiments, the vectors can comprise one or more genes conferring resistance to both eukaryotic and prokaryotic cells. For example, zeocin resistance can be used to select both eukaryotic and prokaryotic cells.

6.3.10 Methods

A number of methods can be used to identify CH3-TM splice acceptor sequence variants that direct the simultaneous expression of membrane-bound and secreted immunoglobulins from a single host cell at different ratios. In some embodiments, a library of dual display vectors comprising a library of CH3-TM splice acceptor sequences is generated and used to transfect a host cell population. The host cell population is cultured in a suitable medium to allow simultaneous expression of membrane-bound immunoglobulin, secreted immunoglobulin, and a membrane-bound marker protein. As controls, host cells are transfected with a vector which generates 100% membrane-bound (e.g., TM vector), or with a vector which generates 100% secreted immunoglobulin (e.g., secretion vector). The TM vector is identical to the dual display vector except that the CH3-TM splice acceptor site is identical to the fully functional CH3 splice acceptor site. During splicing of the primary transcript, the CH2 splice donor site will splice exclusively to the CH3-TM splice acceptor site because the CH3-TM splice acceptor site is closer to the CH2 splice donor site than is the CH3 splice acceptor site. As a result, the TM control vector gives rise to an mRNA which encodes an immunoglobulin having the cell surface tether domain, but not the secreted immunoglobulin. The secretion control vector is identical to the dual display vector, except that there is no intron 4', CH3TM splice acceptor site, or CH3TM exon. As a result, the secretion control vector gives rise to mRNA which encode a secreted immunoglobulin, but not a cell surface-bound immunoglobulin. FACS analysis can be done according to methods known in the art to select and sort transfected host cells expressing membrane-bound antibody and/or membrane-bound marker protein. For example, FACS analysis of cells transfected with the various vectors can be done using labeled antibodies that bind the membrane-bound marker protein and labeled antibodies that bind membrane-bound immunoglobulin protein. FACS analysis of a transfected host cell population transfected with the TM vector will identify transfected host cells expressing membrane-bound immunoglobulin and membrane-bound marker protein in equivalent amounts (see FIG. 2A). FACS analysis of a transfected host cell population transfected with the secretion control vector will identify transfected host cells expressing membrane-bound marker. No significant population of cells expressing membrane-bound immunoglobulin will be identified (see FIG. 2B). When the host cells are transfected with a library of dual display vectors having a diverse array of CH3-TM splice acceptor sequences, FACS analysis will show a decrease in the number of cells expressing membrane-bound immunoglobulin as compared to cells transfected with the TM control vector. Furthermore, quantities of membrane-bound immunoglobulin will be less than that of membrane-bound marker protein (see FIG. 3A). Cells having lower quantities of membrane-bound immunoglobulin as compared to cells transfected with the dual display vector in which the CH3-TM splice acceptor site has not been mutated (the TM vector) are then isolated. The dual display vector is extracted from the cells, and used to transform *E. coli* to obtain sufficient amounts of plasmid for sequence analysis. Methods of plasmid extraction, purification, *E. coli* transformation, and sequencing are well known in the art. In some embodiments, ELISA assays can be used to determine the amount of secreted immunoglobulin generated by the transfected host cells.

A population of recombinant host cells originating from a single clone will comprise individual cells which express the immunoglobulin at different levels. It is desirable to be able to quickly identify and isolate those individual cells that express high levels of immunoglobulins relative to other individual cells. Accordingly, eukaryotic host cells expressing immunoglobulins on the cell surface can be screened to identify and isolate individual cells that express high levels of immunoglobulin.

In some embodiments, eukaryotic host cells are transfected with a dual display vector which comprises polynucleotide sequences encoding heavy and light chain variable and constant domains to produce recombinant eukaryotic host cell.

Eukaryotic host cells can be transformed with the dual display vectors using suitable means and cultured in conventional nutrient media modified as is appropriate for inducing promoters, selecting transformants or detecting expression. Representative examples of such methods include transformation using calcium phosphate precipitation (Dubensky et al., PNAS 81:7529-7533, 1984), lipid mediated transfection (e.g., lipofectamine 2000, Invitrogen), direct microinjection of such nucleic acid molecules into intact target cells (Acsadi et al., Nature 352:815-818, 1991), and electroporation (see also US Patent Publication 2004/0115814 for additional methods for introducing vectors into host cells, incorporated herein by reference in its entirety).

Suitable culture conditions for host cells, such as temperature and pH, are well known. In some embodiments, a titration step can be used to dilute the concentration of plasmid used for cellular transfection to reduce the likelihood of expression in the same cell of multiple vectors encoding different immunoglobulins. Freshney (Culture of Animal Cells, a Manual of Basic Technique, third edition Wiley-Liss, New York (1994)) and the references cited therein provide a general guide to the culture of cells). In other embodiments, the titration step can be omitted.

In some embodiments, transfected host cells displaying expressed immunoglobulins are screened to select those cells expressing high levels of immunoglobulin. Examples of assays suitable for use in the methods described herein include, but are not limited to, magnetic bead sorting and/or fluorescence-activated cell sorting (FACS) can be used to select transfected cells expressing high levels of immunoglobulin. Methods for conducting studies using FACS techniques may be found in, e.g., Shapiro (2002) Practical Flow Cytometry (4th ed.) Wiley & Sons; ISBN: 0471411256; McCarthy and MacEy (eds. 2002) Cytometric Analysis of Cell Phenotype and Function Cambridge Univ. Press; ISBN: 0521660297; Givan (2001) Flow Cytometry: First Principles (2d ed.) Wiley-Liss; ISBN: 0471382248; Radbruch (ed. 2000) Flow Cytometry and Cell Sorting (2d. ed.; Springer Lab Manual) Springer-Verlag; ISBN: 3540656308; and Ormerod (ed. 2000) Flow Cytometry: A Practical Approach (3d. ed.) American Chemical Society; ISBN: 0199638241.

7. EXAMPLES

Example 1

Design of Dual Display Vectors

A dual display vector, as described herein, directs simultaneous expression of two mature mRNA transcripts: one that encodes a membrane-bound immunoglobulin and one that encodes a secreted immunoglobulin. The simultaneous expression of these two transcripts occurs when a single splice donor site (CH2 splice donor site) splices with either the CH3-TM splice acceptor site, or with the CH3 splice acceptor site. The simultaneous expression of the two transcripts requires that the CH3-TM splice acceptor site has been mutated so as to decrease efficiency of splicing with the CH2 splice donor site. Thus, construction of a functional dual display vector requires identification of CH3-TM splice acceptor sites that have this decreased efficiency of splicing with the CH2 splice donor site.

Identification of CH3-TM splice acceptor site sequences that have decreased splicing efficiency as compared to CH3-TM splice acceptor sites without any mutations, required the construction of 3 classes of vectors: 1) class 1, membrane-bound immunoglobulin control vectors, such as pYA400, which directs expression of immunoglobulin protein as the membrane-bound form only; 2) class 2, secreted immunoglobulin control vectors, such as pYA401, which directs expression of immunoglobulin protein as the secreted form only; and 3) class 3, CH3-TM splice acceptor site library vectors, such as YA400 splice library, which contains a diverse array of CH3-TM splice acceptor site sequences and is used to identify CH3-TM splice acceptor site sequences that direct expression of both the membrane-bound and secreted forms of an immunoglobulin. Eukaryotic cells are transformed with one of the three classes of vectors, cultured in appropriate media and conditions to allow immunoglobulin expression, and analyzed via FACS to identify relative levels of surface-bound immunoglobulin expressed by each cell, as described in Example 2.

pYA400 Vector

The pYA400 vector encodes an IgG antibody that recognizes the TMEFF2 protein (Genbank Accession No. NP 057276; see US patent publication No. 2004/0096392, the content of which is incorporated herein by reference in its entirety). pYA400 is illustrated in FIG. 5 and comprises, from a 5' to 3' direction, a CMV promoter operably linked to an exon encoding an immunoglobulin heavy chain variable domain, a second exon encoding an immunoglobulin CH1 domain, a third exon encoding an immunoglobulin hinge domain, a fourth exon encoding an immunoglobulin CH2 domain, a fifth exon encoding a first immunoglobulin heavy chain CH3 domain and a PDGF receptor (PDGFR) transmembrane domain, and a sixth exon encoding a second immunoglobulin heavy chain CH3 domain. The polynucleotide sequence encoding the second immunoglobulin CH3 domain is identical to the polynucleotide sequence encoding the first immunoglobulin heavy chain CH3 domain. The CH2 splice donor site is located adjacent to the 3' end of the fourth exon encoding the immunoglobulin CH2 domain. The CH3-TM splice acceptor site is located adjacent to the 5' end of the fifth exon encoding the immunoglobulin heavy chain CH3 domain and PDGFR-TM domain. The CH3 splice acceptor site is located adjacent to the 5' end of the sixth exon encoding the CH3 domain. Note that in FIG. 5, the polynucleotide encoding the CH3-PDGFR-TM domains is drawn as two exons (arrows), one representing the CH3 sequence and one representing the PDGFR-TM sequence. There is no intervening sequence between the polynucleotides encoding the CH3 and PDGF-TM domains. The polynucleotide sequences encoding the CH3 domain and the PDGFR-TM domain are adjacent and in-frame to one another. The pYA400 dual display vector, depicted in FIG. 5, also has an IRES sequence and a polynucleotide encoding a CD4 protein as a membrane-localized marker protein. This design places expression of the CD4 protein under the control of the same CMV promoter that controls expression of the immunoglobulin heavy chain. As a result, the membrane-localized marker protein functions as an indicator of immunoglobulin expression levels.

The pYA400 dual display vector, depicted in FIG. 5, also has a second CMV promoter operably linked to polynucleotides encoding immunoglobulin light chain variable and constant domains. Thus, the pYA400 dual display vector directs transcription of an mRNA molecule that encodes both a heavy chain immunoglobulin protein and a CD4 marker protein, and transcription of an mRNA molecule that encodes an immunoglobulin light chain domain. Cells transfected with the pYA400 dual display vector, when grown in the appropriate media and conditions, will express intact immunoglobulins having both the heavy and light chains, and the CD4 marker protein.

In the pYA400 vector, the CH2 splice donor site is located adjacent to the 3' end of the CH2 exon and has the sequence GTGGGA. The CH3-TM splice acceptor is located adjacent to the 5' end of the CH3-PDGFR-TM exon, and the CH3 splice acceptor is located adjacent to the 5' end of the CH3 exon. In the pYA400 vector, the CH3-TM and CH3 splice acceptor sites have the same sequence: CTCTGTCCCTACAG (SEQ ID NO: 4). As a result, when eukaryotic cells are transfected with the pYA400 vector, the CH2 splice donor site splices only to the CH3-TM splice acceptor site, because the CH3-TM splice acceptor site is closer to the CH2 splice donor site. All mature mRNA transcripts generated from the pYA400 vector and that encode the immunoglobulin heavy chain, encode the heavy chain immunoglobulin chain having the PDGFR-TM domain. As a result, essentially all immunoglobulins expressed by cells transfected with pYA400 are localized to the cell surface. This vector is used for control FACS and ELISA assays to generate cells that produce immunoglobulin proteins that are 100% membrane-bound.

pYA401 Vector

Figure 6:
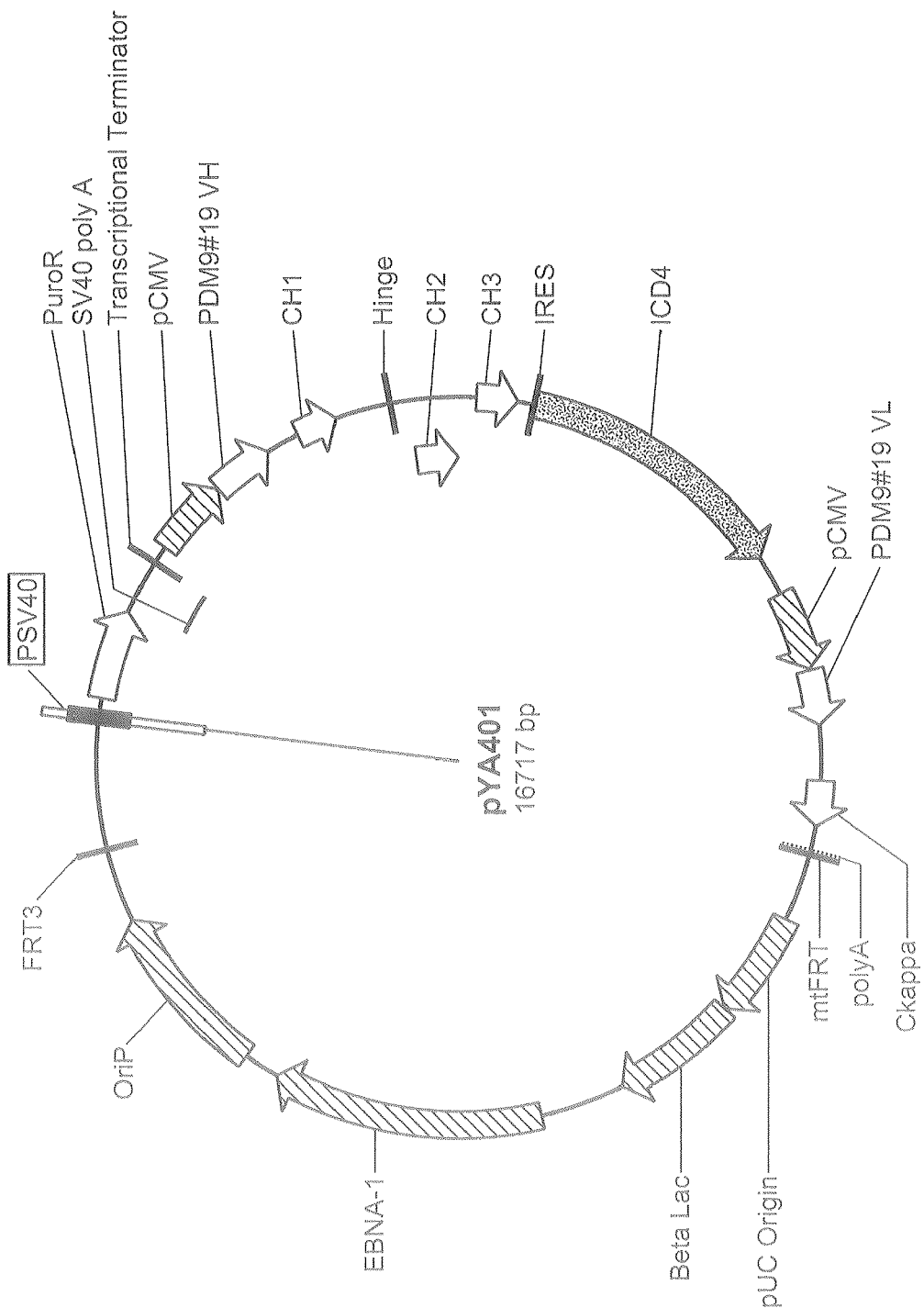
FIG. 6 depicts the pYA401 vector.

The pYA401 display vector is identical to the pYA400 vector except that pYA401 does not have an exon encoding the CH3-TM domain. As shown in FIG. 6, pYA401 comprises from a 5' to 3' direction, a CMV promoter operably linked to an exon encoding an immunoglobulin heavy chain variable domain, a second exon encoding an immunoglobulin CH1 domain, a third exon encoding an immunoglobulin hinge domain, a fourth exon encoding an immunoglobulin CH2 domain, and a fifth exon encoding an immunoglobulin heavy chain CH3 domain. The pYA401 vector does not have an exon encoding a CH3-TM domain. The CH2 splice donor site is located adjacent to the 3' end of the fourth exon encoding the immunoglobulin CH2 domain. The CH3 splice acceptor site is located adjacent to the 5' end of the fifth exon encoding the CH3 domain. The pYA401 vector, depicted in FIG. 6, also has an IRES sequence and a polynucleotide encoding a CD4 protein as a membrane-localized marker protein. The pYA401 display vector, depicted in FIG. 6, also has a second CMV promoter operably linked to a polynucleotide encoding immunoglobulin light chain variable and constant domains. Cells transfected with the pYA401 vector, when grown in the appropriate media and conditions, will express intact immunoglobulins having both the heavy and light chains, and the CD4 marker protein.

In the pYA401 vector, the CH2 splice donor site is located at the 3' end of the CH2 exon and has the sequence GTGGGA. The CH3 splice acceptor is located at the 5' end of the CH3 exon and has the sequence CTCTGTCCCTACAG (SEQ ID NO: 4). As a result, when eukaryotic cells are transfected with the pYA401 vector, the CH2 splice donor site splices to the CH3 acceptor site. All mature mRNA transcripts encoding the immunoglobulin heavy chain domain that are generated from the pYA401 vector encode the heavy chain immunoglobulin CH3 domain having no membrane-localization domain. This vector is used for control FACS and ELISA assays to generate cells that produce immunoglobulin proteins that are 100% secreted.

pYA400 Splice Library Vector

The pYA400 library was constructed to generate a population of dual display vectors that contain a diverse library of CH3-TM splice acceptor sites to be used to transfect host cells. The pYA400 library vector is identical to the pYA400 vector shown in FIG. 5 and described in Section 5.2, except that the CH3-TM splice acceptor site in the pYA400 library vector has the sequence SBSBGBSSSBACAG (SEQ ID NO: 1), wherein B is either G, T, or C and S is either G or C. The non-mutated CH3-TM splice acceptor site (identical to the CH3 splice acceptor site) has the sequence CTCTGTC-CCTACAG (SEQ ID NO: 4). Host cells transfected with the pYA400 library vectors are then cultured in the appropriate media and conditions to express the immunoglobulin and the marker protein. Mutations within the CH3-TM splice acceptor site that decrease efficiency of splicing with the CH2 splice donor site will result in the CH2 splice donor site to sometimes splice with the CH3 splice acceptor site. As the splicing efficiency of the CH3-TM splice site decreases, the frequency of splicing between the CH2 splice donor site and the CH3 splice acceptor site increases, resulting in increased expression of secreted immunoglobulin. The splicing variation has no effect on expression of the CD4 marker protein, which serves as an internal control of expression level directed by the operably linked CMV promoter.

Methods to Construct Display Vectors

At all stages of vector construction, generated PCR products were initially cloned into PCR4-TOPO® vector (Invitrogen) for sequence verification. Fragments were excised from verified clones with relevant restriction enzymes for sub-cloning into vector.

Generation of the dual display vector was done using the pCEP4 plasmid (Invitrogen), an Epstein-Barr virus (EBV)-derived plasmid containing the oriP and the full-length EBNA-1 gene. The polynucleotide sequences encoding heavy and light chain immunoglobulin proteins were derived from vector PDM9#19 (see, e.g., U.S. Publication No. 2004/0096392, the content of which is incorporated herein by reference in its entirety), which has a polynucleotide encoding the heavy and light chains of an IgG antibody that recognizes the TMEFF2 protein.

Construction of pYA400

The variable heavy region with 5' splice site from PDM9#19 was generated by PCR from vector HT3.0 PDM9#19 with the addition of restriction sites EaeI and PacI at 5', and XhoI, EcoRI, BglII, SacI, BstBI at 3' with primers 10320 (ATTTGGCCATTAATTAACACCATGGCT-GTCCTGGGGCTGCTTCTCTGC (SEQ ID NO: 7)) and 10321 (TCGAATTCCTCGAGGCCATTCTTACCT-GAGGAGACGGTGACC (SEQ ID NO: 8)) followed by primers 10320 and 10322 (AGGTTCGAAGAGCTCA-GATCTGAATTCCTCGAGGCCATTCTTACCTGAGG (SEQ ID NO: 9)) and sub-cloned into the 9.193 Kb NotI/BstBI digest fragment of pYA209, generating pYA400-step 1.

Partial PDM9#19 constant heavy region from intron 1 through first 65 bp of intron 4 was generated by PCR from vector HT3.0 PDM9#19 with the addition restriction sites XhoI at 5' and EcoRI at 3' using primers 10323 (ATTCTC-GAGGCTTTCTGGGGCAGGCCAGGCCTGACC (SEQ ID NO: 10)) and 10324 (ATTGAATTCCTCAGGGCA-GAGGGTGGGCCGAGC (SEQ ID NO: 11)) and sub-cloned into XhoI/EcoRI digest of pYA400-step 1 to give pYA400-step 2.

A PCR construct containing an EcoRI site, the remaining 35 bp of intron 4 and exon 5 of PDM9#19, the PDGFR-transmembrane domain from vector AE20 BCR4 and intron 4 of PDM9#19 with BglII site was made in three overlapping PCR segments using primers 10325 (AGGAATTCAGAGT-GACCGCTGTACCAACC (SEQ ID NO: 12)) and reverse primer 10326 (TCCTGCGTGTCCTGGCCCACAGCTT-TACCCGGAGACAGGGAGAGG (SEQ ID NO: 13)) to give PCR product 1 off HT3.0 PDM9#19.

Primer 10327 (TCTCCCTGTCTCCGGGTAAAGCT-GTGGGCCAGGACACGCAGGAGG (SEQ ID NO: 14)) and reverse primer 10328 (AGCGGGGGCTTGCCGGC-CGTCGCCTAACGTGGCTTCTTCTGC (SEQ ID NO 15)) were used to generate PCR product 2 off AE20 BCR4.

Primer 10329 (TTGGCAGAAGAAGCCACGTTAGGC-GACGGCCGGCAAGCC (SEQ ID NO: 16)) and reverse primer 10330 (ATTAGATCTAGGGCAGCGCTGGGT-GCTTTATTTCC (SEQ ID NO: 17)) off HT3.0 PDM9#19 to give PCR product 3.

PCR products 1, 2 and 3 were combined by PCR with primers 10325 and 10330, followed by PCR using primers 10325 and primer 10461 (ATTAGATCTTACGTGCCAAG-CATCCTCGTGC (SEQ ID NO: 18)) and sub-cloned into EcoRI/BglII digest of pYA400-step 2 to give pYA400-step 3.

A fragment having Exon 5 of PDM9#19 including a polyA site and restriction sites BglII at the 5' end and SacI at 3' end was generated by PCR using primers 10331 (ATTA-GATCTCCCGTGGGGTGCGAGGGCCACATGG (SEQ ID NO: 19)) and 10332 (ATTGAGCTCAGGGCA GCGCTGGGTGC (SEQ ID NO: 20)) and HT3.0 PDM9#19 as the template DNA, and sub-cloned into a BglII/SacI digest of pYA400-step 3 to give pYA400-step 4.

An IRES-CD4 fragment with a SacI restriction site at the 5' end and a BstBI at the 3' end was generated by PCR using the NEF39 FoxP3 HA ICD4 vector with primers 10333 (AT-TGAGCTCCGGACCGCTAATTCCGG (SEQ ID NO: 21)) and 10334 (AGGTTCGAACTCATTAAACTTGTATTT-TAATGG (SEQ ID NO: 22)). The PCR product was sub-cloned into a SacI/BstBI digest of pYA400-step 4 to give pYA400-step 5.

A DNA fragment having the PDM9#19 light chain with CMV promoter at the 5' end and restriction site BstBI at both the 5' and 3' ends was PCR-amplified in three overlapping segments using primers 10347 (AGGTTCGAAAGGCGT-TACATAACTTACG (SEQ ID NO: 23)) and 10348 (ATC-CATGGTGGCCTGCAGGGGATCTGAGTC-CGGTAGCGCTAGC (SEQ ID NO: 24)) with pYA209 as the template DNA to generate the CMV promoter sequence, PCR product 1.

Primers 10349 (ACTCAGATCCCCTGCAGGCCAC-CATGGATTTTCAGGTGC (SEQ ID NO: 25)) and 10350 (TCAGAGTTTAGAATTGCGGCCGCTTAG-GAAAGTGCACTTACG (SEQ ID NO: 26)) were used with HT3.0 PDM9#19 as the template DNA to generate a fragment having the PDM9#19 variable light region, PCR product 2.

Primers 10351 (AGTGCACTTTCCTAAGCGGCCG-CAATTCTAAACTCTGAGGGGGTCG (SEQ ID NO: 27)) and 10352 (AGGTTCGAAGTGCAAAGATTCACTT-TATTTATTC (SEQ ID NO: 28)) were used with HT3.0 PDM9#19 as the template DNA to generate a fragment having the PDM9#19 Ckappa region, PCR product 3.

PCR products 1, 2 and 3 were combined by PCR with primers 10347 and 10352 to give PCR product 4 and sub-cloned into the BstBI digested vector of pYA400-step 5 to give pYA400-step 6.

The mtFRT site was added by primer extension to PCR product 4 using primers 10415 (TTCGGAATAGGAACT-TCGTGCAAAGATTCACTTTATTTATTC (SEQ ID NO: 29)), 10416 (TACCTTTTGAAGAATAGGAACTTCG-GAATAGGAACTTCGTGC (SEQ ID NO: 30)) and 10417 (AGGTTCGAAGTTCCTATACCTTTTGAAGAATAGG (SEQ ID NO: 31)). This final product sub-cloned into the BstBI digest of pYA400-step 6 to give pYA400-step 7.

A FRT site with restriction sites SpeI at 5' end and EcoRV at 3' end generated by PCR and primer extension from pYA400-step 4 with forward primer 10418 (ATTACTAGTATTTAT-TGCCCAAGG (SEQ ID NO: 32)) and reverse primers 10419 (AACTTCGGAATAGGAACTTTCCCACCCCATGAG CTGTCACG (SEQ ID NO: 33)), 10420 (TACTAAGTA-GAGAATAGGAACTTCGGAATAGGAACTTTCC (SEQ ID NO: 34)) and 10421 (ATTGATATCGAAGTTCCTATAC-TAAGTAGAGAATAGG (SEQ ID NO: 35)) and sub-cloned into a SpeI/EcoRV digest of pYA400-step 7 to give the final vector pYA400.

Construction of pYA401

Plasmid pYA401 is the dual expression control vector described herein which does not comprise a CH3-TM exon. The pYA401 vector is used for control FACS and ELISA assays to generate cells that produce immunoglobulin proteins that are 100% secreted. PDM9#19 exon 5 through the polyA site and partial IRES with restriction sites EcoRI at 5' end and BstBI at 3' end was generated by PCR from the 15.8 Kb EcoRI/BglII digest fragment of pYA400 using primers 10463 (ATTGAATTCAGAGTGACCGCTGTACCAACC (SEQ ID NO: 36)) and 10464 (ATTAAGCTTCCAGAG-GAACTGCTTCC (SEQ ID NO: 37)) and sub-cloned into the 15062 bp fragment of a EcoRI/HindIII digest of pYA400.

Construction of PYA400 Library Having Mutated CH3-TM Acceptor Splice Site Sequences The pYA400 library vector is the pYA400 vector as described above, but which further comprises the CH3-TM splice acceptor site (between EcoRI and BglII restriction sites) engineered to allow any T position in the splice site to be T, G, or C, and any G positions to be a G or C, and was generated by PCR using degenerate primers (see FIG. 4). The pYA400 library vector is the pYA400 vector as described above, but which further comprises The CH3-TM splice acceptor site (between EcoRI and BglII restriction sites) was engineered to allow at any T position in the splice site to be T, G or C, and any G position to be a G or C was generated by PCR by the use of degenerate primers (see FIG. 4). The library was generated by successive rounds of PCR from an initial PCR product template using primers 10406 (ACAGGGCAGCCCCGAGAACCACAGG (SEQ ID NO: 38)) and primer 10330 (ATTAGATCT AGGG CAGCGCTGGGTGCTTTATTTCC (SEQ ID NO: 17)), followed by primers 10407 (AACSBSBGBSSSBA-CAGGGCAGCCCCGAGAACCACAGG (SEQ ID NO: 39)) and 10330, followed by primers 10408 (AGAGTGACCGCT-GTACCAACSBSBGBSSSBACAGGGCAGCC (SEQ ID NO: 40)) and 10330, followed by primers 10409 (AGGAAT-TCAGAGTGACCGCTGTACCAAC (SEQ ID NO: 41)) and 10330, followed by primers 10325 (AGGAATTCAGAGT-GACCGCTGTACCAACC (SEQ ID NO: 12)) and 10461 (ATTAGATCTTACGTGCCAAGCATCCTCGTGC (SEQ ID NO: 18)).

The final PCR product was sub-cloned into both pCR®4-TOPO® vector (Invitrogen) and pCR®4Blunt TOPO® vector (Invitrogen) to give an approximately 60-fold library. The required 573 bp fragment was removed from library with restriction enzymes EcoRI and BglII and sub-cloned into 15.8 Kb fragment of EcoRI/BglII digest of pYA400 to give an approx 10-fold over sampled library.

Example 2

FACS Analysis of the CH3-TM Splice Acceptor Sequence Library

FACS analysis of cells transfected with the pYA400, pYA401 or pYA400 library vectors was done to identify CH3-TM splice acceptor sites within the pYA400 library vectors that directed expression of a reduced ratio of membrane-bound to secreted immunoglobulin expression. Cells transfected with pYA400 library vector and expressing decreased levels of surface-bound immunoglobulin as compared to cells transfected with the pYA400 vector are identified and selected by FACS. Vectors are isolated from these selected cells and sequenced to identify the mutations within the CH3-TM splice acceptor sequence as described in Example 3.

In all FACS analysis of cells transfected with the dual display vectors, expression of the CD4 marker protein is measured as an internal control. Because CD4 transcription is controlled by the same CMV promoter that regulates transcription of the immunoglobulin heavy chain gene, CD4 expression levels are a strong indicator of overall immunoglobulin expression levels.

Methods for FACS Analysis

A human embryonic kidney-derived cell line 293c18 (American Type Culture Collection, Manassas, Va.) was maintained in DME medium supplemented with 10% fetal bovine serum (FBS; HyClone, Logan, Utah) and 0.25 mg/ml G418 at 37° C. in a 7.5% $CO_2$ incubator. Library transfection was performed as follows for the pYA400 vector, the pYA400 library, and the pYA401 vector.

Transfection was performed by premixing 1 µg of library DNA with 100 µg of pACY184/ER2400 carrier plasmid (New England Biolabs, Beverly, Mass.). The DNA mixture was diluted into 6 ml of Hybridoma-SFM (Invitrogen). Separately, 250 µl of Lipofectamine 2000 (Invitrogen) was diluted with 6 ml of Hybridoma-SFM, and then combined with diluted DNA mixture. After 20 min incubation at RT, the DNA-Lipofectamine mixture was added to culture media of $2.5 \times 10^7$ 293c18 cells in poly-D-lysine coated T75 flasks. Two days after transfection, 0.8 mg/ml puromycin was added to the growth medium. Under this condition, approximately $2.5 \times 10^5$ independent stable transfectants were obtained.

To select for cells that displayed immunoglobulin on the cell surface and that also expressed secreted immunoglobulin, approximately $10^7$ 298c18 stable transfected cells were incubated with Goat-anti-Human Kappa-RPE (Southern Biotech) and Anti-mouse CD4-APC (BD BioSciences) at 1 µg/ml for 1 hr at 4° C. After washing with FACS buffer (PBS+1% FBS) three times, stained cells were sorted on a MoFlo MLS (DakoCytomation, Glostrup, Denmark). Sorted cells were grown in DME medium containing 10% FBS, 0.8 µg/ml puromycin and 0.25 mg/ml G418, and analyzed by FACS staining using a FACSCalibur flow cytometer with CellQuest software (BD Biosciences).

Results of FACS Analysis

Figure 3A:
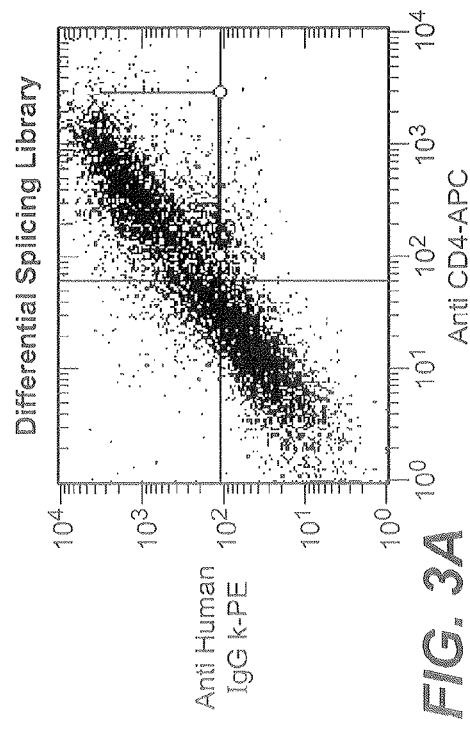
FIGS. 3A-3B depict FACS analysis of cells transfected with: A) pYA400 library and B) pYA400 library after a first FACS sort.
Figure 3B:
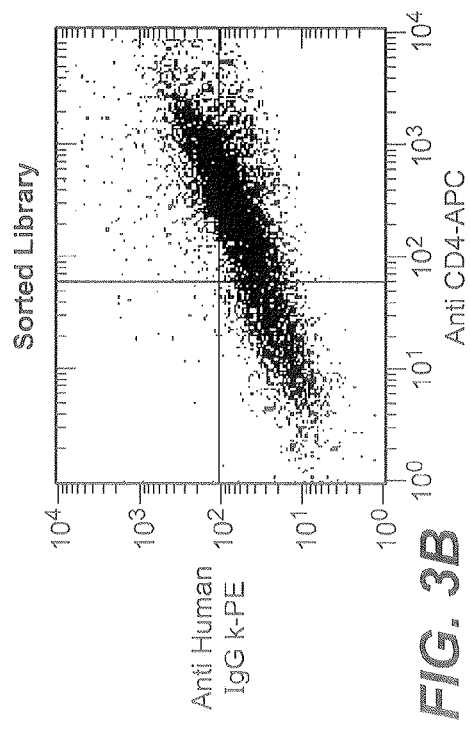
Figure 2A:
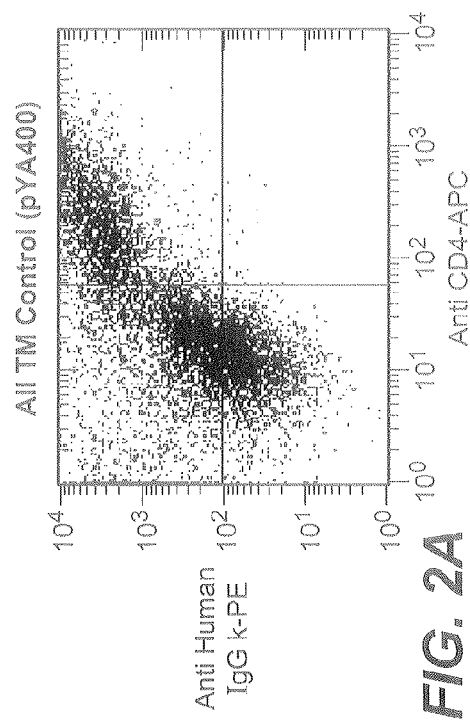
Figure 2B:
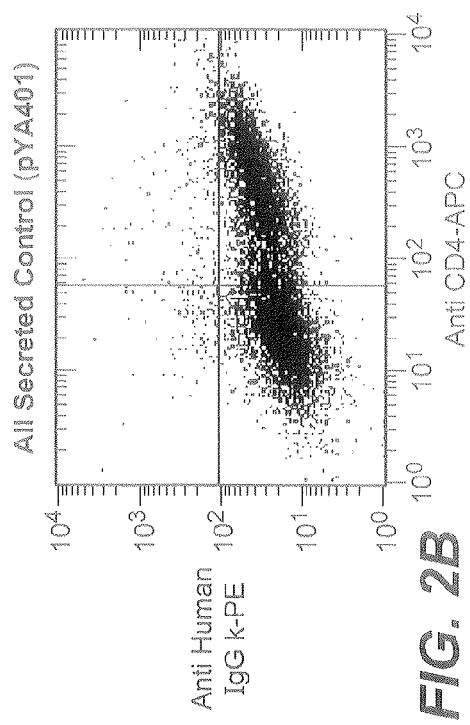

In the FACS analysis using two color staining of the transfected cells, pYA400 transfected cells showed cell surface-displayed human IgG1 equal to cell surface displayed CD4 as shown in FIG. 2A, while PYA401 showed only background level of transmembrane staining and same level of CD4 staining as show in FIG. 2B. The pYA400 library transfected cells showed less surface displayed IgG1 signal but maintained similar level of CD4 expression as shown in FIG. 3A. A subpopulation of cells that display lower quantities of cell surface displayed IgG was selected as shown by the triangle in FIG. 3A and subsequently sorted. FACS staining confirmed the selection of cells that expressed surface-bound IgG as compared to the pYA400 control vector, as evidenced by the lower shifted staining (FIG. 3B).

Example 3

Sequencing of CH3-TM Mutations

After the FACS sort to select for cells showed decreased levels of cell surface bound immunoglobulin, sorted cells were plated in CloneMatrix semi solid media (Genetix, UK) with Fluorecein conjugated affinity pure goat anti human IgG1 Fcγ F(ab')2 fragment (Jackson Immuno Research Inc) at 1000 cell/ml. Cells were incubated for 7 days. Use of Clone-Pix (Genetix, UK) to pick clones showed relatively high expression of secreted human IgG1. After single clones were recovered in 96 well, cells were expanded into 6 well plates in DME medium containing 10% FBS, 0.8 ng/ml puromycin and 0.25 mg/ml G418. Plasmid DNA was extracted using buffers in the QIAprep Spin Miniprep Kit (Qiagen, Valencia, Calif.). Approximately $10^7$ cells washed with PBS were resuspended in 500 µl of P1 buffer containing RNase A and lysed with 500 µl of P2 buffer. After 5 min of incubation at room temperature, 700 µl of N3 buffer was added. The cell lysate was centrifuged for 10 min and the supernatant was extracted with phenol-chloroform, and then precipitated in ethanol. The recovered DNA was digested with DpnI to eliminate plasmid that did not replicated in 293c18 cells. Subsequently, ElectroMax DH5α-E cells (Invitrogen) was transformed with DpnI-digested plasmid by electroporation. Single bacteria colonies were cultured in 2 ml LB broth with 50 µg/ml carbenicillin overnight. Plasmid DNA was then purified using QIAprep Spin Miniprep Kit (Qiagen, Valencia, Calif.). Sequencing was carried out using PDL in house sequencing facility.

The results of the sequencing reactions are shown in FIG. 4, and show CH3-TM splice acceptor site sequences that were present in individual transfected cells identified by FACS analysis as expressing decreased levels of surface-localized immunoglobulin as compared to transfected cells having the TM control vector (pYA400). FIG. 4 shows the wild-type CH3-TM splice acceptor site sequence at the top of the table. Note that the 3' residues of the splice acceptor site sequence, ACAG, were not varied in construction of the pYA400 library. This ensured that the location of splicing would always occur at the same location regardless of variations in other positions of the splice acceptor site.

The pYA400 splice acceptor site sequences were randomly mutated in such a way as to increase the number of G's and reduce the number of C's and T's within the splice acceptor site sequences. The central G (shaded) was not mutated as it is critical for splicing to occur.

The sequencing results presented in FIG. 4 show that in each case, there is an increase in the number of G's as compared to the wildtype CH3-TM splice acceptor site sequence. Specifically, the splice acceptor site sequence in the FACS selected clones each comprised at least 3 G's, in addition to the central G that was not varied. In three of the sequenced splice acceptor sites, there were at least 8 G's in the mutated region.

Example 4

ELISA Analysis of the Secreted IgG1 from Cells Selected from FACS Analysis

To show that the dual display vectors directing decreased ratios of membrane-bound to secreted immunoglobulin expression express high amounts of secreted immunoglobulin, ELISA assays are done.

To determine human IgG1 secretion, $1 \times 10^6$ cells from the selected clones as shown in FIG. 3A are washed once and plated in DME medium containing 10% FBS, 0.25 mg/ml G418 and 0.8 µg/ml puromycin 12 well cell culture plates. Supernatant is collected after 24 hours of incubation and an ELISA assay is performed to measure the secreted IgG.

MaxiSorp™ plates (Nalge Nunc, Rochester, N.Y.) are coated overnight at 4° C. with AffiniPure Goat Anti-Human IgG, Fcγ Fragment Specific (min X Bov,Hrs,Ms Sr Prot) (Jackson Immuno Research Laboratory Inc) at 1 µg/ml in PBS. Plates are then blocked with SuperBlock Blocking Buffer (Pierce, Rockford. IL) for 30 minutes and washed with washing buffer (PBS containing 0.1% Tween 20). Samples and standards diluted in 100 µl ELISA buffer (PBS containing 1% BSA and 0.1% Tween 20) are added to wells and incubated for 1 hour at room temperature. After washing, HRP-conjugated goat anti-human IgG antibodies (Southern Biotechnology Associates Inc) diluted 1:5000 in ELISA buffer is added. After 1 hour of incubation, plates are washed and bound antibodies are detected by addition TMB 1 component HRP microwell substrate (BioFx Laboratories, Owings Mills, Md.). The reaction is terminated by addition of 100 µl/well of $2NH_2SO_4$ and the absorbance is measured at or 450 nm using a VERSAmax microplate reader (Molecular Devices, Sunnyvale, Calif.).

Example 5

Screening and Analysis of Dual Display Vectors

293c18 cells were transfected with a differential display library. After 15 day of selection on puromycin; cells were stained with anti-human IgG-PE and anti-mouse CD4-APC. A population with low IgG surface expression but positive CD4 expression was sorted by MoFlo. The sorted population was sub cloned into single clones. Sixty seven cell clones were expanded and screened for surface IgG expression and secreted IgG expression. All of the 67 clones had low IgG secretion.

A second screening strategy using ClonPix was also used to screen the dual display vectors. For this strategy, the population was selected and sorted as described above. Single cell colonies were selected from the sorted population. Forty two single cell clones were chosen for further analysis based on high IgG secretion as determined using ClonePix. These clones were expanded and screened for surface IgG expression. Twelve clones were chosen based on the criteria of low surface IgG expression and high secreted IgG expression. Plasmids from the twelve clones were recovered by DNA miniprep. E. coli Top 10 cell were transformed with the recovered plasmids by electroporation. Six transformed bacteria clones from each cell clone were picked and grow overnight for DNA miniprep and sequencing. The sequencing results indicated that these clones contain higher percentage of G.

Figure 7:
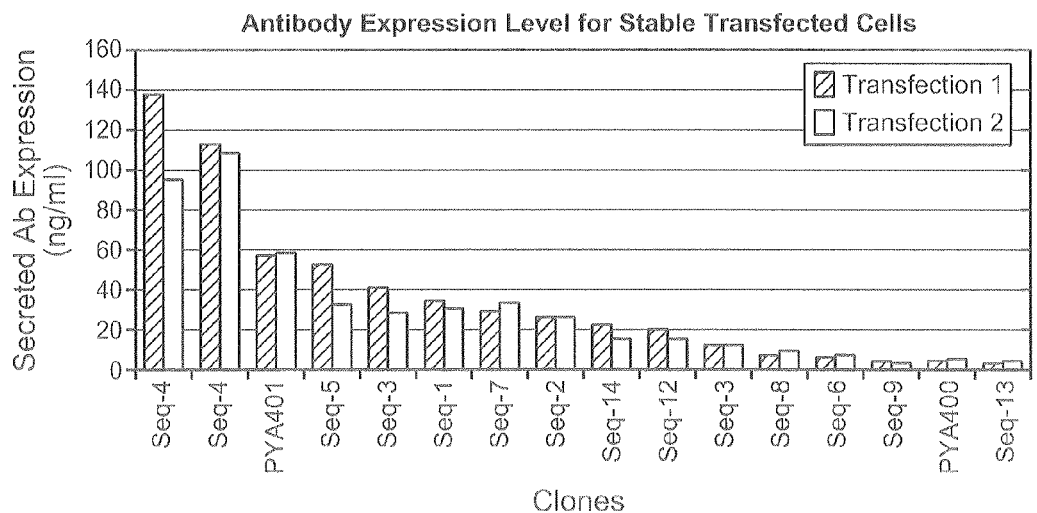
FIG. 7 depicts production of secreted antibodies from stably transfected cells.

The DNA was recovered from each of the sequenced E. coli clones and used to transfect 293c18 cells. After puromycin selection for 14 days, 1,000,000 transfected cells were plated in 24 well cell culture plates. The supernatants were collect after 24 hours incubation and analyzed by ELISA for secreted IgG levels. The clone containing sequence 4 showed highest level of secreted IgG expression and was chosen for further analysis (see FIG. 7).

Figure 8:
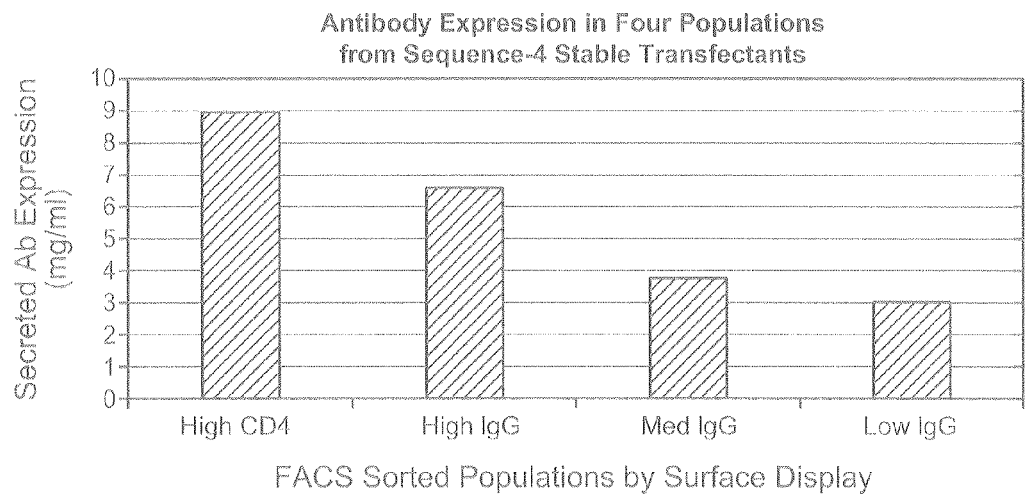
FIG. 8 depicts the correlation between antibody expression on the surface and secreted by stably transfected cells.

The DNA from the clone containing sequence 4 has the OriP and EBNA genes, which when expressed maintain the plasmid as a separate entity inside the cell without integration. Because expression plasmids are typically integrated into the transfected cell genome following transfection of stable cell lines, the oriP gene and a portion of the EBNA gene were removed. The resulting plasmid DNA was used to transfect 293S cell to generate stable integrated cell lines. After three weeks of puromycin selection, the cells were sorted into four populations based on surface display. These four populations were: 1) high CD4 expression; 2) high IgG expression; 3) mid IgG expression; and 4) low IgG expression. These four populations were expanded and 1,000,000 cells were seeded in to culture plates. After 7 days of incubation, the supernatants were collected and analyzed by IgG capturing ELISA. ELISA showed the secreted IgG level correlated well with the surface expression level (see FIG. 8). These results suggest that surface displayed IgG can be used as a sorting index for the selection of transfected cells which secrete high secreted levels of IgG. The high CD4 surface display population also showed higher level of IgG secretion in this experiment, suggesting CD4 may also be used as an indicator for screening for transfected cells with high levels of IgG secretion.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method for identifying recombinant cells expressing a cell surface immunoglobulin comprising:

transfecting eukaryotic host cells with an expression vector comprising in a 5' to 3' direction:

a promoter;

a first exon encoding an immunoglobulin heavy chain variable domain;

a second exon encoding an immunoglobulin CH1 domain;

a third exon encoding an immunoglobulin hinge domain;

a fourth exon encoding an immunoglobulin CH2 domain;

a fifth exon encoding a first immunoglobulin heavy chain CH3 domain and a cell surface tether domain;

a sixth exon encoding a second immunoglobulin heavy chain CH3 domain, wherein the polynucleotide sequence encoding said second immunoglobulin CH3 domain is identical to the polynucleotide sequence encoding said first immunoglobulin heavy chain CH3 domain;

a CH2 splice donor site located adjacent to the 3' end of said fourth exon encoding the immunoglobulin CH2;

a CH3-TM splice acceptor site located adjacent to the 5' end of said fifth exon encoding the immunoglobulin heavy chain CH3 domain and a cell surface tether domain;

a CH3 splice acceptor site located adjacent to the 5' end of said sixth exon encoding the second immunoglobulin heavy chain CH3 domain;

wherein said CH2 splice donor site splices alternatively to:

said CH3-TM splice acceptor site to form a first spliced transcript, for producing a membrane-bound immunoglobulin; or said CH3 splice acceptor site to form a second spliced transcript, for producing a secreted immunoglobulin;

and selecting recombinant cells that specifically bind a target antigen.

2. The method of claim 1, wherein said recombinant cells are selected for target antigen binding using florescence-activated or bead-based sorting.

3. The method of claim 1, wherein said eukaryotic host cells are selected from the group consisting of CHO, NS0, COS, 293-HEK, Jurkat, Raji, Daudi, CV-1, PerC6, SP2.0, and HeLa cells.

4. The method of claim 1, wherein said vector further comprises an IRES element and a polynucleotide encoding a heterologous marker protein.

5. The method of claim 4, wherein said IRES element and said polynucleotide encoding a heterologous marker protein are located downstream of said sixth exon.

6. The method of claim 4, wherein said polynucleotide encoding a heterologous marker protein and said IRES element are located upstream of said first exon and downstream of said promoter.

7. The method of claim 1, wherein said cell surface tether domain is selected from the group consisting of platelet derived growth factor receptor (PDGF-R) transmembrane domain, B7-1 transmembrane domain, asialoglycoprotein receptor (ASGPR) transmembrane domain and glycosidylphosphatidylinositol (GPI) signal domain.

8. The method of claim 1, wherein said vector further comprises a second promoter operatively linked to a polynucleotide sequence encoding an immunoglobulin light chain variable domain and a polynucleotide sequence encoding an immunoglobulin light chain constant domain.

9. The method of claim 1, wherein said CH3-TM splice acceptor site comprises the sequence SBSBGBSSSBACAG (SEQ ID NO: 1), wherein B is either G, T, or C, and S is either G or C.

10. The method of claim 1, wherein said vector further comprises a first recombinase site located upstream of the polynucleotide sequences which encode the immunoglobulin heavy chain constant and variable domains and a second recombinase site located downstream of the polynucleotide sequence which encodes the second immunoglobulin heavy chain CH3 domain.

11. The method of claim 1, wherein said promoter is the cytomegalovirus (CMV) promoter.

12. The method of claim 1, wherein said vector further comprises an Epstein-Barr virus replication origin (OriP).

13. The method of claim 1, wherein said vector further comprises a polynucleotide sequence encoding an Epstein-Barr Nuclear Antigen 1 (EBNA-1) protein.

14. The method of claim 1, wherein said vector further comprises a drug resistance gene selected from the group consisting of a puromycin resistance gene, a neomycin resistance gene, a hygromycin gene, a xanthine-guanine phosphoribosyltransferase gene (gpt), a zeocin resistance gene, and a blasticidin resistance gene.

15. The method of claim 1, wherein said vector further comprises a prokaryotic origin of replication.

* * * * *